(12) United States Patent
Mueckter et al.

(10) Patent No.: US 10,034,696 B2
(45) Date of Patent: Jul. 31, 2018

(54) IMPLANT SYSTEM FOR BONE FIXATION

(75) Inventors: Helmut Mueckter, Aachen (DE); Ingo Stoltenberg, Probsteierhagen (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 113 days.

(21) Appl. No.: 13/983,841

(22) PCT Filed: Feb. 8, 2012

(86) PCT No.: PCT/EP2012/000577
§ 371 (c)(1),
(2), (4) Date: Nov. 7, 2013

(87) PCT Pub. No.: WO2012/107226
PCT Pub. Date: Aug. 16, 2012

(65) Prior Publication Data
US 2014/0058392 A1    Feb. 27, 2014

(30) Foreign Application Priority Data

Feb. 8, 2011   (WO) .......................... EP2011/000585

(51) Int. Cl.
*A61B 17/56* (2006.01)
*A61B 17/72* (2006.01)
*A61B 17/74* (2006.01)

(52) U.S. Cl.
CPC ........ *A61B 17/725* (2013.01); *A61B 17/7233* (2013.01); *A61B 17/744* (2013.01)

(58) Field of Classification Search
CPC ..... A61B 17/72; A61B 17/725; A61B 17/744; A61B 17/7225; A61B 17/7233; A61B 17/7241; A61B 17/7283; A61B 17/68
(Continued)

(56) References Cited

U.S. PATENT DOCUMENTS 3,433,220 A    3/1969   Zickel
4,776,330 A   10/1988   Chapman et al.
(Continued)

FOREIGN PATENT DOCUMENTS

EP    0838199 A1    4/1998
EP    1175872 A2    1/2002
(Continued)

OTHER PUBLICATIONS

Gamma3 Long Nail R2, Copyright date 2004, pp. 1-52.
(Continued)

*Primary Examiner* — Jacqueline Johanas
*Assistant Examiner* — Tessa Matthews
(74) *Attorney, Agent, or Firm* — Lerner, David, Littenberg, Krumholz & Mentlik, LLP

(57)   ABSTRACT

An implant system for use in orthopedic surgery for fixation of bone includes an intramedullary nail and a coupling unit. The intramedullary nail has a medial side, a lateral side and a proximal portion defining a longitudinal axis. The proximal portion includes a bore defining a first axis substantially parallel to the longitudinal axis of the proximal portion and a transverse bore configured to receive a bone fastener. The coupling unit is movably arranged within the bore of the proximal portion and includes one or more bone fastener engagement members at one or both of the lateral side and the medial side of the intramedullary nail.

30 Claims, 12 Drawing Sheets

(58) Field of Classification Search
USPC .................................................. 606/62–68
See application file for complete search history.

(56) References Cited

U.S. PATENT DOCUMENTS

| | | | |
|---|---|---|---|
| 5,032,125 A * | 7/1991 | Durham et al. ............... 606/62 |
| 5,176,681 A | 1/1993 | Lawes et al. |
| 6,221,074 B1 | 4/2001 | Cole et al. |
| 6,296,645 B1 | 10/2001 | Hover et al. |
| 6,402,753 B1 | 6/2002 | Cole et al. |
| 6,406,477 B1 | 6/2002 | Fujiwara |
| 6,648,889 B2 | 11/2003 | Bramlet et al. |
| 6,835,197 B2 | 12/2004 | Roth et al. |
| 6,855,146 B2 | 2/2005 | Frigg et al. |
| 6,921,400 B2 | 7/2005 | Sohngen |
| 6,926,719 B2 | 8/2005 | Sohngen et al. |
| 7,018,380 B2 | 3/2006 | Cole |
| 7,041,104 B1 | 5/2006 | Cole et al. |
| 7,182,765 B2 | 2/2007 | Roth et al. |
| 7,306,600 B2 * | 12/2007 | Roth et al. ...................... 606/53 |
| 7,591,819 B2 | 9/2009 | Zander et al. |
| 7,763,023 B2 | 7/2010 | Gotfried |
| 7,867,231 B2 | 1/2011 | Cole |
| 8,092,454 B2 | 1/2012 | Sohngen |
| 8,100,911 B2 | 1/2012 | Yamazaki et al. |
| 8,157,801 B2 | 4/2012 | Doubler et al. |
| 8,157,802 B2 | 4/2012 | Elghazaly et al. |
| 8,172,841 B2 * | 5/2012 | Defossez ........................ 606/64 |
| 8,303,590 B2 | 11/2012 | Elghazaly et al. |
| 8,808,293 B2 | 8/2014 | Buettler et al. |
| 8,840,675 B2 | 9/2014 | Song |
| 2002/0032445 A1 | 3/2002 | Fujiwara |
| 2002/0107578 A1 | 8/2002 | Speitling et al. |
| 2002/0156473 A1 | 10/2002 | Bramlet et al. |
| 2005/0069397 A1 | 3/2005 | Shavit et al. |
| 2005/0143739 A1 * | 6/2005 | Shinjo .................. A61B 17/744 606/62 |
| 2005/0203510 A1 * | 9/2005 | Sohngen .............. A61B 17/744 606/60 |
| 2006/0156473 A1 | 7/2006 | Chambers et al. |
| 2006/0200160 A1 * | 9/2006 | Border et al. .................. 606/88 |
| 2007/0049938 A1 | 3/2007 | Wallace et al. |
| 2007/0233100 A1 | 10/2007 | Metzinger |
| 2008/0140077 A1 | 6/2008 | Kebaish |
| 2008/0294164 A1 | 11/2008 | Frank et al. |
| 2008/0294203 A1 * | 11/2008 | Kovach et al. ............... 606/308 |
| 2009/0048600 A1 | 2/2009 | Matityahu et al. |
| 2010/0249781 A1 * | 9/2010 | Haidukewych et al. ....... 606/62 |
| 2010/0249852 A1 * | 9/2010 | Brumfield et al. ........... 606/282 |
| 2011/0054474 A1 | 3/2011 | Metzinger et al. |
| 2011/0196372 A1 | 8/2011 | Murase |
| 2012/0197255 A1 | 8/2012 | Elghazaly |
| 2012/0253410 A1 | 10/2012 | Taylor et al. |
| 2013/0041414 A1 | 2/2013 | Epperly et al. |
| 2013/0158601 A1 | 6/2013 | Stone et al. |
| 2014/0012259 A1 | 1/2014 | Matityahu et al. |
| 2014/0058392 A1 | 2/2014 | Mueckter et al. |
| 2014/0088595 A1 | 3/2014 | Mueckter et al. |
| 2014/0094802 A1 | 4/2014 | Simon et al. |
| 2014/0330174 A1 | 11/2014 | Warlick et al. |

FOREIGN PATENT DOCUMENTS

| | | | |
|---|---|---|---|
| EP | 1547534 A2 | 6/2005 |
| JP | H02-21859 A | 1/1990 |
| JP | 2005205201 A | 8/2005 |
| JP | 2009148318 A | 7/2009 |
| KR | 100953149 B1 | 4/2010 |
| WO | 02098330 A2 | 12/2002 |
| WO | 03032852 A2 | 4/2003 |
| WO | 03094763 A1 | 11/2003 |
| WO | 2012107056 A1 | 8/2012 |

OTHER PUBLICATIONS

Heineman, et al., "Intra-abdominal Migration of a Lag Screw in Gamma Nailing: Report of a Case", J Orthop Trauma, Dec. 2010, vol. 24, No. 12, pp. e119-e122.

Horas, et al., "Mediate Schenkelhalsschraubendislokation nach Gammanagelosteosynthese einer pertrochantaren Femurmetastase", 2008, p. 746-748 (English translation of Abstract provided).

Li, et al., "Medical pelvic migration of the lag screw in a short gamma nail after hip fracture fixation: a case report and review of the literature", Journal of Orthopaedic Surgery and Research, 2010, 5:62, pp. 1-7.

Synthes, "Titanium Trochanteric Fixation Nail System-Screw Option. For intramedullary fixation of proximal femur fractures.", Copyright date 2010, pp. 1-67.

International Search Report for Application No. PCT/EP2012/000577 dated May 31, 2012.

International Search Report for Application No. PCT/EP2011/000585 dated Jun. 27, 2011.

European Examination Report for Application No. 12705227.2 dated May 5, 2015.

Japanese Office Action for Application No. 2013-552885 dated Aug. 25, 2015.

* cited by examiner

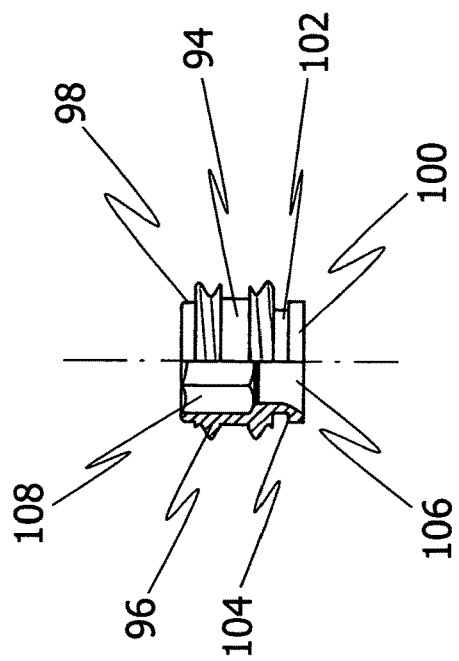
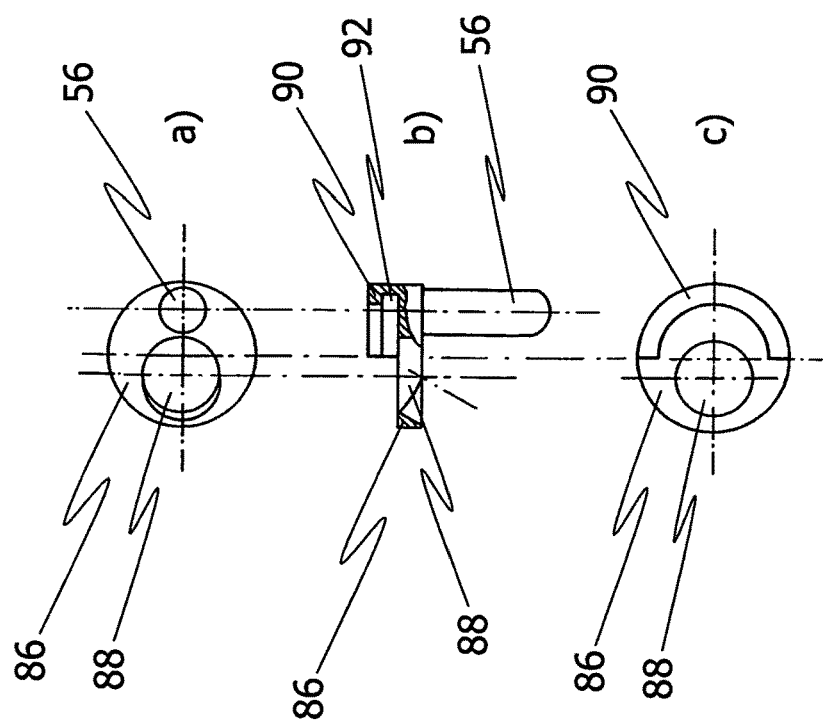
Fig. 5
Fig. 4

IMPLANT SYSTEM FOR BONE FIXATION

CROSS-REFERENCE TO RELATED APPLICATIONS

The present application is a national phase entry under U.S.C. § 371 of International Application No. PCT/EP2012/000577 filed Feb. 8, 2012, published in English, which claims priority from International Application No. PCT/EP2011/000585 filed Feb. 8, 2011, all of which are incorporated herein by reference.

BACKGROUND OF THE INVENTION

The present disclosure generally relates to an implant system for use in orthopaedic surgery. Specifically, the disclosure relates to an intramedullary nail for internal fixation of bone, such as a femur.

Femur fractures commonly occur in the femoral neck and the trochanteric regions. Typically, trochanteric and subtrochanteric femur fractures are currently treated with an intramedullary nail having a transverse bore to receive a bone fastener, such as a femoral neck screw usually provided in the form of a lag screw. The intramedullary nail is fitted in the intramedullary canal of the femur and the lag screw passes through the transverse bore of the intramedullary nail, through the neck of the femur and into the femoral head.

The lag screw is designed to transfer the load of the femoral head into the nail shaft by bridging the fracture line to allow fast and secure fracture healing. Further, the lag screw is allowed to slide in the intramedullary nail in accordance with the sintering of the femoral fracture. Typically, a set screw is inserted into a bore of the intramedullary nail to prevent a rotation and an uncontrolled medial deviation of the lag screw.

The intramedullary nail may include a central cannulation along its longitudinal axis for receiving a surgical wire (guide wire), such as a Kirschner-wire. The surgical wire is inserted into the marrow cavity of the femur prior to the insertion of the intramedullary nail.

U.S. Pat. No. 5,176,681 A relates to an intramedullary intertrochanteric fracture fixation appliance and fitting device. The intramedullary fracture fixation appliance comprises an intramedullary nail having a transverse bore for receiving a femoral neck screw in the form of a lag screw. The proximal end of the intramedullary nail is provided with another bore extending co-axially through the nail and opening into the transverse bore. A set screw is located within the co-axial bore of the nail. The lower end of the set screw has a centrally arranged protrusion. When the set screw is in its final position, the central protrusion of the set screw engages in one of longitudinally extending grooves arranged on the shaft of the lag screw.

U.S. Pat. No. 6,835,197 relates to an intramedullary nail with a coupling mechanism. The coupling mechanism includes a body member and a flat prong laterally extending from the body member. Further, a short bolt for threadable engagement with a partially threaded channel that extends axially in the intramedullary nail is rotatably coupled to the body member. The body member further includes tabs, which are received in grooves of the channel, such that cooperation between the tabs and the grooves prevents rotation of the body member within the channel. When the body member is urged toward a lag screw inserted through a transverse bore of the intramedullary nail, the flat prong contacts a side surface of the lag screw and fills a void defined by the flat portion of the lag screw, such that the prong fits tightly in the space between the channel wall and the lag screw.

U.S. Pat. No. 6,648,889 B2 relates to an intramedullary nail with a bifurcated lock. Similar to the body member described in U.S. Pat. No. 6,835,197 B2, a sleeve lock includes two lateral locking tabs in the form of flat prongs and an anti-rotation tab engaging within a groove of a channel of the intramedullary nail. The locking tabs of the sleeve lock engage within locking slots of a sleeve which is arranged on the lag screw.

U.S. Pat. No. 6,406,477 B1 relates to an intramedullary nail having a set hole in its proximal portion. The proximal portion of the nail further has two transverse bores in which a lag screw and an auxiliary connector are to be located. Since the auxiliary connector extends through the nail at a location between a set screw screwed into the set hole of the intramedullary nail and the lag screw, a spacer for transmitting a clamping force is interposed between the set screw and the lag screw. The spacer includes a body and two apart legs laterally extending from the body. When the set screw is placed on the spacer in the set hole and is screwed into the set hole, the set screw pushes the entire spacer down and the lower ends of the legs engage within grooves of the lag screw. The auxiliary connector is positioned between the two legs of the spacer and is securely held by a central boss formed at the forward end of the set screw and inserted through an opening formed in the body of the spacer.

US 2006/0200160 A1 discloses a coupling arrangement between an intramedullary nail and a lag screw. A coupling assembly includes an engagement member and an engagement driver. The coupling assembly is received in a proximal portion of a bore of the intramedullary nail for engaging a portion of the lag screw that is located within a transverse bore of the intramedullary nail. The engagement driver is threadably coupled with the intramedullary bore of the nail and operates to move the engagement member between a disengaged position and an engaged position. The engagement member includes two engagement arms formed as flat prongs which can engage the lag screw when the engagement member is in the engaged position.

Further technological background can be found in EP 1 175 872 A2 (U.S. Pat. No. 6,046,477) and EP 1 547 534 A2 (U.S. Pat. No. 7,601,153).

The conventional intramedullary nails have several drawbacks. A set screw without a through hole cannot be preassembled with the intramedullary nail and thus has to be inserted into the intramedullary nail intraoperatively after removal of a guide wire. In this case, the insertion of the relatively small set screw into the shaft of the intramedullary nail is cumbersome. Soft tissue overlapping the opening at the proximal end of the nail may hinder the insertion of the set screw and the mutual engagement of the threads. Thus, the set screw may get stuck within the intramedullary nail and the operation time increases due to additional operation steps. Moreover, a set screw having one or more prongs cannot prevent an uncontrolled medial deviation of the lag screw. Hence, the construct of intramedullary nail, coupling assembly and lag screw inserted through the transverse bore of the intramedullary nail and into bone can therefore not provide a high mechanical load stability within the body of the patient. Additionally, using set screws with prongs requires a modification of the current lag screw shaft design providing longitudinal extending grooves in which a pin of the set screw can engage to guarantee a defined sliding of the lag screw within the intramedullary nail.

BRIEF SUMMARY OF THE INVENTION

Aspects of the present disclosure are directed to providing an implant system simplifying and facilitating the surgical procedure and implantation of an intramedullary nail and corresponding bone fasteners, as well as providing a sufficient mechanical load construct stability within the body of a patient.

According to a first aspect, there is provided an implant system for use in orthopaedic surgery for fixation of bone. The implant system comprises an intramedullary nail with a medial side, a lateral side and a proximal portion defining a longitudinal axis. The proximal portion includes a bore defining a first axis substantially parallel to the longitudinal axis of the proximal portion and at least one transverse bore configured to receive a bone fastener. Further, the implant system comprises a coupling unit configured to be movably arranged within the bore of the proximal portion and including one or more bone fastener engagement members at one or both of the lateral side and the medial side of the intramedullary nail.

The proximal portion may be adapted to guide the coupling unit with the one or more bone fastener engagement members in a direction substantially parallel to the longitudinal axis of the proximal portion. The guidance may be such that the one or more bone fastener engagement members can engage a bone fastener penetrating the transverse bore of the proximal portion (at one or both of the lateral side and the medial side of the intramedullary nail). The transverse bore of the proximal portion of the intramedullary nail may be formed as an angulated or oblique bore having a defined angle with respect to the longitudinal axis of the proximal portion. In one case, the one or more bone fastener engagement members may be located at opposite sides with respect to a line which is substantially perpendicular to a longitudinal axis of the bone fastener. In other words, the one or more bone fastener engagement members may be located at opposite sides with respect to a line defined by the anterior side and the posterior side of the intramedullary nail.

In one implementation, the proximal portion may include one or more guiding structures for the coupling unit, each defining a second axis substantially parallel to the longitudinal axis of the proximal portion. The one or more guiding structures may be configured to slidably receive the one or more bone fastener engagement members (or any other portion of the coupling unit) at one or both of the lateral side and the medial side of the intramedullary nail or at another side thereof. The second axes of the one or more guiding structures may be oriented eccentrically with respect to the longitudinal axis of the proximal portion.

The bore of the proximal portion and the one or more guiding structures may be arranged adjacent to each other, for example, adjacent in transverse direction (e.g., in lateral-medial-direction). The bore of the proximal portion of the intramedullary nail can be arranged co-axially. Further, the bore of the proximal portion of the intramedullary nail may be located at the medial side or at the lateral side of the intramedullary nail or is centrally located with respect to the longitudinal axis of the proximal portion. The bore of the proximal portion of the intramedullary nail and the one or more guiding structures may thus be oriented eccentrically with respect to the longitudinal axis of the proximal portion of the intramedullary nail. The one or more guiding structures may be located at one or both of the lateral side and the medial side of the intramedullary nail.

The one or more guiding structures can be formed as grooves or bores. The one or more guiding structures may, for example, have a V-, U- or C-shape or the like in cross-section. Alternatively, the one or more guiding structures may have a round (e.g., circular), square (e.g., quadrangular, trapezoidal, quadrat or rectangle) or triangular shape or the like in cross section.

The coupling unit may include at least a first bone fastener engagement member located at the lateral side of the intramedullary nail and a second bone fastener engagement member located at the medial side. In such an implementation, the first and second bone fastener engagement members may have different lengths. For example, the bone fastener engagement member on the lateral side may be longer than the bone fastener engagement member on the opposite side. In one implementation, the first and second bone fastener engagement members are interconnected by a base member. The base member and the bone fastener engagement members may constitute a one-piece structure.

In another realization, the coupling unit may include a first bone fastener engagement member and a second bone fastener engagement member which lie on a line that extends perpendicularly to a plane including the longitudinal axis of the proximal portion and a longitudinal axis of the transverse bore. The line may be spaced apart from the longitudinal axis of the proximal portion in one of a lateral direction and a medial direction of the intramedullary nail (i.e., the two bone fastener engagement members may both be located at one of the lateral side and the medial side of the intramedullary nail). In certain other implementations, the line may cross the longitudinal axis of the proximal portion.

The coupling unit may be configured to urge, upon moving of the coupling unit toward a distal portion of the intramedullary nail, the one or more bone fastener engagement members in the direction of the longitudinal axis of the proximal portion towards the distal portion. In such a case the one or more bone fastener engagement members may engage within a groove or any other structure of the bone fastener to prevent rotation of the bone fastener about a longitudinal axis of the bone fastener.

In one implementation, the one or more bone fastener engagement members may define a longitudinal axis intersecting a longitudinal axis of the bone fastener. The one or more bone fastener engagement members may each be formed as a blade, a prong or a bolt having a shaft (and an optional tip with a spherical ball, circular, cone, flat, U, or V shape). The one or more bone fastener engagement members may have a round (e.g., circular), square (e.g., quadrangular, trapezoidal, quadrat or rectangular) or triangle shape or the like in cross-section. Further, the one or more bone fastener engagement members can be eccentrically arranged on a drive member of the coupling unit.

In one realization, the coupling unit may include a drive member for moving the coupling unit within the bore of the proximal portion. The drive member may or may not include a through hole for receiving a surgical wire. Further, the through hole of the drive member may be arranged centrally. The drive member may be movably connected to the one or more bone fastener engagement members.

The intramedullary nail may include a channel substantially along a longitudinal axis of the intramedullary nail. The channel of the nail may have a circular or angular shape in cross-section. A cannulation can be defined through the intramedullary nail by the channel of the intramedullary nail, the through hole of the drive member and the bore of the proximal portion of the intramedullary nail, such that a surgical wire may be inserted through the cannulation. The surgical wire may be a guide wire, such as a Kirschner-wire or any other kind of wire.

In one implementation, the drive member may have an external thread for threadable engagement with the intramedullary nail, for example with the proximal portion of the intramedullary nail. The drive member can further include a ring (made of, for example, synthetic material) arranged in a circumferential groove of the drive member. Alternatively, the ring may be arranged on the external thread of the drive member (e.g., in a groove of the external thread). The material of the ring may be deformable. Thus, the ring can be a deformable plastic ring. The bore of the proximal portion of the intramedullary nail may include an internal thread, wherein the external thread of the drive member can mate with the internal thread of the proximal portion. Further, the drive member may be formed as a (short) bolt.

The drive member may include a drive transmitting portion, and the one or more bone fastener engagement members may include a groove substantially arranged in a direction transverse to the longitudinal direction of the one or more bone fastener engagement members. The drive transmitting portion can be configured to movably engage within the groove of the one or more bone fastener engagement members (e.g., such that rotation of the drive member may cause movement of the one or more bone fastener engagement members in the direction of the longitudinal axis of the proximal portion of the intramedullary nail). The drive transmitting portion may be rotatably supported in the groove of the one or more bone fastener engagement members.

In another implementation, the drive member may include a drive transmitting portion, and the one or more bone fastener engagement members may be arranged on a base member, wherein the drive transmitting portion can movably engage the base member. In one realization, the base member may have a holding portion, wherein the drive transmitting portion can movably engage with the holding portion. Rotation of the drive member may cause movement of the one or more bone fastener engagement members in the direction of the longitudinal axis of the proximal portion of the intramedullary nail.

The base member may include a through hole for receiving a surgical wire. The base member may have a circular shape and the through hole may be oriented centrally or eccentrically. Further, the channel of the intramedullary nail, the bore of the proximal portion of the intramedullary nail, the through hole of the base member, the through hole of the drive member and a central bore of the proximal portion can define a cannulation, such that a surgical wire may be inserted through the cannulation.

The implant system may further comprise a retainer arranged in the proximal portion of the intramedullary nail, wherein the range of motion of the coupling unit in the proximal direction can be limited by the retainer. The retainer may be formed as a snap ring or spring ring having a defined spring constant. The retainer can further have a circular shape.

The implant system may comprise the bone fastener. The bone fastener can be formed as a sliding screw, a lag screw or femoral neck screw or any kind of blade. The bone fastener may comprise one or more grooves or other structures, and the one or more bone fastener engagement members may be configured to engage within the one or more grooves or other structures of the bone fastener to prevent rotation of the bone fastener about a longitudinal axis of the bone fastener.

The coupling unit may be captively held within the proximal portion of the intramedullary nail. Moreover, the drive member and the one or more bone fastener engagement members may be preassembled within the proximal portion of the intramedullary nail. The drive member may be movably connected to one or more bone fastener engagement members.

Also provided is an implant system for use in orthopaedic surgery for fixation of bone, comprising an intramedullary nail with a proximal portion defining a longitudinal axis, wherein the proximal portion includes a bore defining a first axis substantially parallel to the longitudinal axis of the proximal portion and at least one transverse bore, a bone fastener configured to penetrate the transverse bore and having at least one groove with one or more ramps, and a coupling unit configured to be movably arranged within the bore of the proximal portion and including one or more bone fastener engagement members configured to engage the at least one groove and to exert pressure on the bone fastener via the one or more ramps.

According to a further aspect there is provided a method of fracture fixation of bone, the method comprising the steps inserting an intramedullary nail with a medial side and a lateral side into a marrow cavity of bone, wherein the intramedullary nail comprises a proximal portion defining a longitudinal axis, wherein the proximal portion includes a bore defining a first axis substantially parallel to the longitudinal axis of the proximal portion and a transverse bore configured to receive a bone fastener, and a coupling unit movably arranged within the bore of the proximal portion and including one or more bone fastener engagement members at one or both of the lateral side and the medial side of the intramedullary nail; inserting a bone fastener through the transverse bore of the proximal portion of the intramedullary nail into bone for stabilization of the bone fracture; and driving the coupling unit for producing an engagement of the one or more bone fastener engagement members with the bone fastener penetrating the transverse bore of the intramedullary nail, thereby preventing rotation of the bone fastener.

The method may further comprise an initial step of inserting a guide wire into the marrow cavity of bone, wherein the intramedullary nail is cannulated and inserted over the guide wire into the marrow cavity of bone. In a further step, the guide wire may be removed after insertion of the intramedullary nail.

When the bore and the one or more guiding structures of the proximal portion of the intramedullary nail are spaced apart from each other, and the coupling unit, for example, in form of a set screw, includes one or more bone fastener engagement members and a drive member with a through hole, wherein the one or more guiding structures slidably receive the one or more bone fastener engagement members, the coupling unit (i.e., the one or more bone fastener engagement members and the drive member) can be preassembled or preloaded within the intramedullary nail, while allowing simultaneous passage of a surgical wire. In particular, the surgical procedure and the implantation of the intramedullary nail within an intramedullary canal of a femur is simplified and facilitated. Further, due to the fact that the one or more bone fastener engagement members are at one or both of the lateral side and the medial side of the intramedullary nail, the construct of intramedullary nail, coupling unit and bone fastener inserted through the transverse bore of the intramedullary nail and into bone provides a high mechanical load stability within the body of the patient. Moreover, modifications of the current bone fastener design are not necessarily required.

BRIEF DESCRIPTION OF THE DRAWINGS

These and other features, aspects and advantages of the present disclosure will become more apparent from the following detailed description taken in conjunction with the accompanying drawings, wherein:

FIG. 4 shows top, side and bottom views of an alternative pin embodiment;

FIG. 5 is a side view of an alternative drive member embodiment;

DETAILED DESCRIPTION

Figure 1:
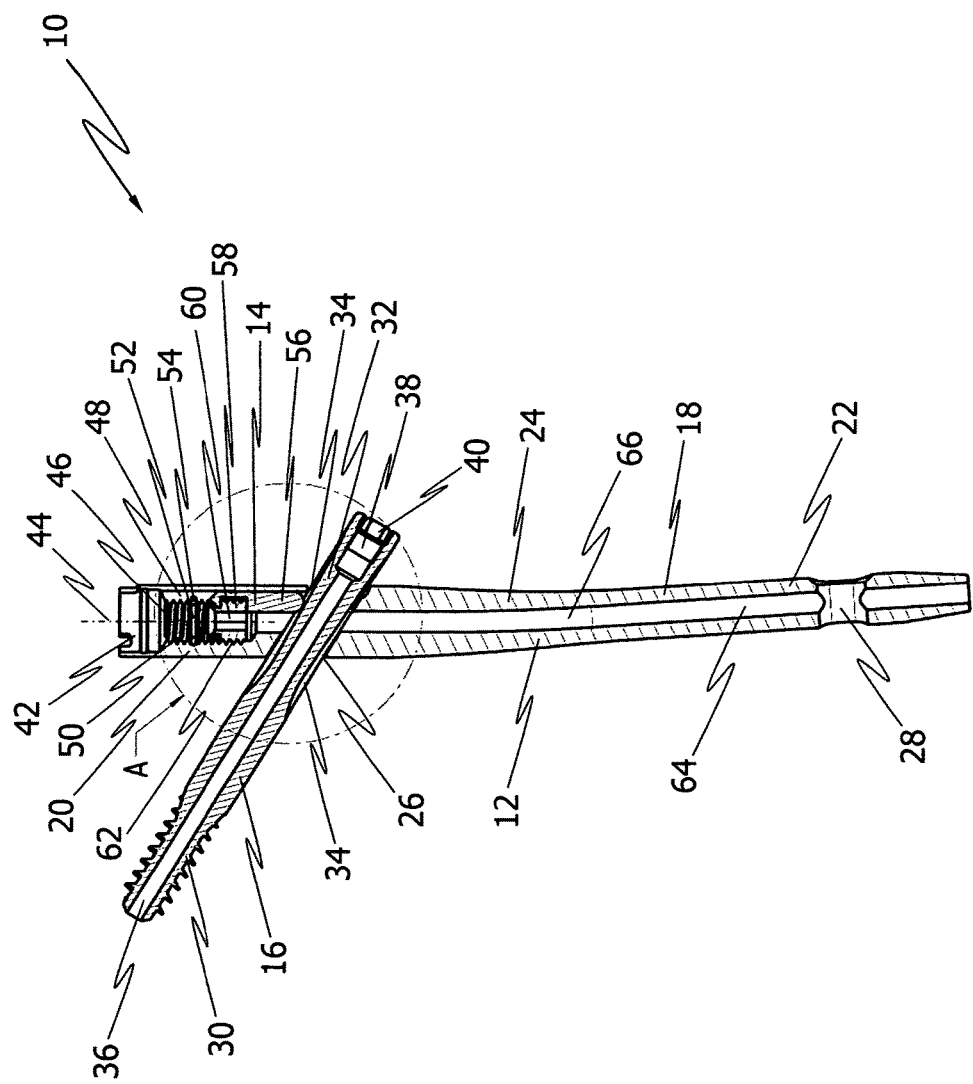
FIG. 1 is a cross-sectional view of an implant system embodiment.

In the following description of exemplary embodiments, the same or similar components will be denoted by identical reference numerals. It will be appreciated that certain components of different configurations may interchangeably be provided in different embodiments. It will further be appreciated that while the following embodiments will primarily be described with respect to the treatment of a femur, the implant system presented herein can also be used for other treatments.

Referring to FIG. 1, there is shown a cross-sectional view of an embodiment of an implant system 10 for use in orthopaedic surgery for fixation of bone, such as a femur (not shown in FIG. 1). The implant system 10 comprises an intramedullary nail 12, a coupling unit 14 and a bone fastener 16. The coupling unit 14 couples the bone fastener 16 to the intramedullary nail 12. The intramedullary nail 12 includes a rod-shaped body 18 insertable into the inner cavity (marrow cavity) of the femur, i.e., into the intramedullary canal of the femur. The rod-shaped body 18 of the intramedullary nail 12 includes a proximal portion 20, a distal portion 22 which is longer than the proximal portion 20, and a bent portion 24 located between the proximal portion 20 and the distal portion 22. In other words, the bent portion 24 connects the proximal portion 20 and the distal portion 22.

As shown in FIG. 1, the intramedullary nail 12 includes a transverse bore 26 located at the proximal portion 20. An axis of the transverse bore 26 has an angle with respect to a longitudinal axis of the intramedullary nail, such that a longitudinal axis of the transverse bore 26 has an oblique extension relative to an axial extension of the proximal portion 20. While in the present embodiment only a single transverse bore 26 is utilized, in other embodiments multiple (e.g., two or more) transverse bores may be provided in the proximal portion 20.

The proximal portion 20 of the intramedullary nail 12 has a diameter sufficient to accommodate the transverse bore 26 therein, while the distal portion 22 of the intramedullary nail 12 has a smaller diameter with respect to the proximal portion 20, adapted to the shape of the marrow cavity of the femur in order to facilitate the insertion of the distal portion 22 into the intramedullary canal. Further, the distal portion 22 includes a through hole 28 extending orthogonally to a longitudinal axis of the distal portion 22. The through hole 28 is formed at an end of the distal portion 22 of the intramedullary nail 12 for receiving a bone fastener, such as a locking screw, in order to securely fix the intramedullary nail 12 to bone.

In the embodiment of the implant system 10 shown in FIG. 1, the bone fastener 16 is a femoral neck screw in the form of a lag screw 16. The lag screw 16 is adapted to penetrate the transverse bore 26 of the intramedullary nail 12. The lag screw has a front portion 30 including a thread, for example a coarse thread, and a rear portion 32. The rear portion 32 is provided with a plurality of longitudinally extending grooves 34 (two are shown in FIG. 1) arranged on the peripheral surface of the rear shaft portion 32 along the axis of the lag screw 16. Typically, four grooves 34 are disposed on the peripheral surface of the lag screw 16 at intervals of 90° around the longitudinal axis of the lag screw 16. Each groove 34 defines a ramp having a shallow end and a deeper end. The rising ramp extends from the shallow end at a rear end of the rear portion 32 towards the threaded front portion 30 to the deeper end. The grooves 34 thus have an asymmetric depth profile. Further, the lag screw 16 includes a central cannulation 36 along the longitudinal axis of the lag screw 16. The rear portion 32 of the lag screw 16 includes at the rear end a co-axial bore 38 and a recess 40 (e.g., a hexalobular internal driving feature) for receiving a screw driver or a wrench (e.g., in the form of a entrainer driving feature).

As illustrated in FIG. 1, the proximal portion 20 of the intramedullary nail 12 includes a recess 42 for receiving an end cap or a tool, such as a holding instrument or targeting instrument (not shown in FIG. 1) at the upper end of the proximal portion 20. The proximal portion 20 defines a longitudinal axis 44 and further includes a bore 46 and a guiding structure 48. In the present embodiment, the bore 46 of the proximal portion 20 is co-axial with the longitudinal axis 44 of the proximal portion 20. As further shown in FIG. 1, the bore 46 includes an internal thread 50 and a recess portion 52 for receiving a retainer 54 the exemplary in form of a snap ring.

The coupling unit 14 is preassembled and movably arranged within the proximal portion 20 of the intramedullary nail 12. The coupling unit 14 includes one bone fastener engagement member 56 and a drive member 58 with a through hole 60. The engagement member 56 is located at a lateral side of the intramedullary nail 12 and realized in the exemplary form of a substantially cylindrical bolt or pin 56.

The terms medial and lateral are standard anatomical terms of direction and denote a direction toward the center or median plane of a body and the opposite direction from the center to the side, respectively. With respect to the overall present disclosure and the exemplary embodiments, the medial and lateral directions may generally lie within a plane including the longitudinal axis 44 of the proximal portion 20 and a longitudinal axis of the transverse bore 26. In such a case, the medial side of the intramedullary nail 12 may be a side facing towards the outgoing side of the transverse bore 26 (e.g., towards a tip of the bone fastener 16 penetrating the transverse bore 26), whereas the lateral side may be a side facing towards ingoing side of the transverse bore 26 (e.g., towards a head of the bone fastener 16). In many cases, the intramedullary nail 12 will be anatomically adapted so that the nail 12 inherently defines the medial and lateral sides, for example with respect to one or more its bending (e.g., as embodied by bent portion 24), an inclination of the transverse bore 26, and so on.

Returning to FIG. 1, the drive member 58 is movably connected to the pin 56. The through hole 60 of the drive member 58 is a central through hole having an axis which coincides with the longitudinal axis 44 of the proximal portion 20. The drive member 58 further includes an external thread 62 for threadable engagement with the intramedullary nail 12 (e.g., with the proximal portion 20 as shown in FIG. 1). The internal thread 50 of the proximal portion 20 mates with the external thread 62 of the drive member 58. In the present embodiment, the drive member 58 of the coupling unit 14 is movably arranged within the bore of the proximal portion 20 of the intramedullary nail 12. Moreover, the coupling unit 14 is captively held within the proximal portion 20 of the intramedullary nail 12. As also illustrated in FIG. 1, the guiding structure 48 slidably receives the pin 56 of the coupling unit 14, such that the pin can engage within a groove 34 of the lag screw 16. Upon engagement within the groove 34, the pin 56 can exert pressure on the lag screw 16 for stabilization purposes. The pressure is initially zero or low enough to still permit a sliding movement of the lag screw 16 relative to the intramedullary nail 12. The pressure will change (and typically increase) as the lag screw slides due to the depth profile (i.e., the laterally and medially provided ramps) of the grooves 34.

As further shown in FIG. 1, the intramedullary nail 12 includes a channel 64 substantially along the longitudinal axis of the intramedullary nail 12. Thus, a cannulation 66 is defined through the intramedullary nail 12 by the channel 64 of the intramedullary nail 12, the through hole 60 of the drive member and the bore 46 of the proximal portion 20, such that a surgical wire (not shown in FIG. 1) can be inserted through the cannulation 66.

Figure 2:
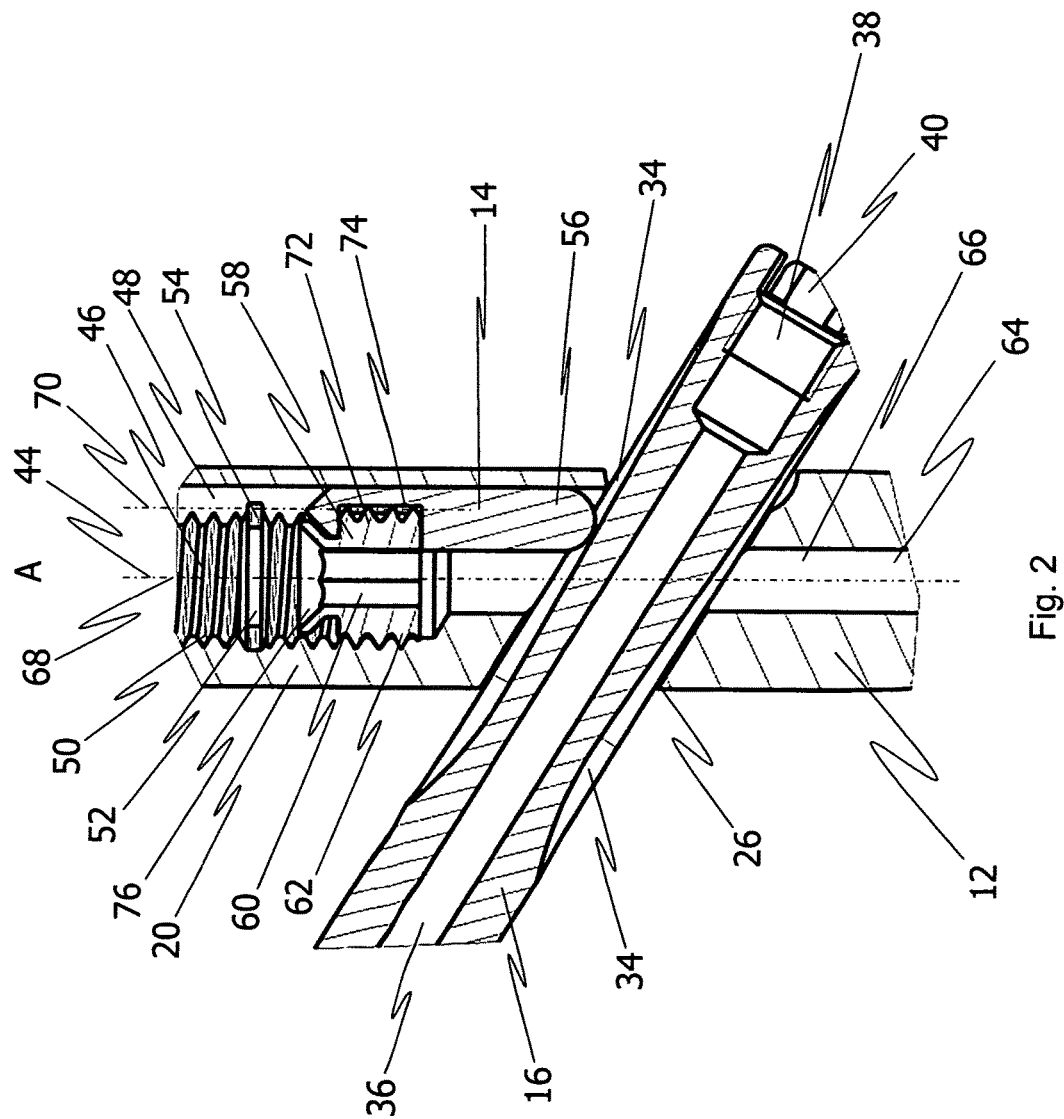
FIG. 2 is a detailed view of a proximal portion of the implant system embodiment shown in FIG. 1.

FIG. 2 illustrates a detailed view A of the proximal portion 20 of the intramedullary nail 12 shown in FIG. 1. As shown in FIG. 2, the bore 46 of the proximal portion 20 defines a first axis 68 which, in the present embodiment, coincides with the longitudinal axis 44 of the proximal portion 20. In other embodiments, the first axis 68 of the bore 46 may be spaced apart from and extend parallel to the longitudinal axis 44 of the proximal portion 20. In certain cases, the first axis 68 of the bore 46 may be slightly inclined (e.g., at an angle of up to 10° or 15°) with respect to the longitudinal axis 44 of the proximal portion 20 and thus remain at least substantially parallel thereto.

Further, the guiding structure 48 defines a second axis 70. The first axis 68 of the bore 46 and the second axis 70 of the guiding structure 48 are substantially parallel to the longitudinal axis 44 of the proximal portion 20 of the intramedullary nail 12 and are spaced apart from each other. Moreover, the second axis 70 of the guiding structure 48 is oriented eccentrically with respect to the longitudinal axis 44 of the proximal portion 20. The bore 46 of the proximal portion and the guiding structure 48 are thus arranged adjacent to each other. In the present embodiment illustrated in FIGS. 1 and 2, the bore 46 of the proximal portion 20 is located centrally and the guiding structure 48 of the proximal portion 20 is located at the lateral side of the intramedullary nail 12. The pin 56 of the coupling unit 14 guided within the guiding structure 48 is therefore arranged at the lateral side of the intramedullary nail 12. The bore 46 of the proximal portion 20 terminates at its lower end in the channel 64 of the intramedullary nail 12. The guiding structure 48 terminates at its lower end in the transverse bore 26 of the proximal portion 20. In the present embodiment, the term "lower end" means that end which is nearer to the distal portion 22 of the intramedullary nail 12, and the term "upper end" is the opposite of the lower end. Further, the guiding structure 48 is formed as a groove having a circular shape (e.g., C-shape) in cross-section.

As also illustrated in FIG. 2, the pin 56 of the coupling unit 14 is eccentrically arranged on the drive member 58, i.e., arranged at an eccentric position (e.g., at a lateral position as shown in FIG. 2). Further, the guiding structure 48 and thus the pin 56 define a longitudinal axis intersecting the longitudinal axis of the lag screw 16. The pin 56 is formed as a bolt having a cylindrical shaft (here: with circular cylindrical cross-section) and a spherical tip at its lower end.

The drive member 58 includes a drive transmitting portion 72 for transmitting the movement of the drive member 58 to the pin 56. The pin includes a groove 74 at its upper end. The groove 74 of the pin 56 is substantially arranged in a direction transverse to the longitudinal direction of the pin 56. The drive transmitting portion 72 of the drive member 58 movably engages within the groove 74 of the pin 56. For this purpose, the drive transmitting portion 72 is rotatably supported in the groove 74 of the pin 56. Thus, rotation of the drive member 58 causes movement of the pin 56 in the direction of the longitudinal axis 44 of the proximal portion 20.

The drive member 58 of the coupling unit 14 has a receiving portion 76 in form of a cone having a recess (e.g., in the form of a hexalobular internal driving feature) for receiving a tool, screwdriver, wrench or the like. By driving the drive member 58 using such a tool, the entire coupling unit 14 moves along the longitudinal axis 44 of the proximal portion 20 of the intramedullary nail 12, since the external thread 62 of the drive member 58 mates with the internal thread 50 of the bore 46 of the proximal portion 20. In other words, the position of the coupling unit 14, and therewith the position of its pin 56, within the proximal portion 20 of the intramedullary nail 12 can be adjusted by screwing the drive member 54 of the coupling unit 14 along the longitudinal axis 44.

As shown in FIG. 2, the range of motion (i.e., the movement) of the coupling unit 14 in the proximal direction is limited by the retainer 54. The retainer 54 in form of a snap ring engages within the recess portion 52. The recess portion 52 is formed as a circumferential groove within the proximal portion 20 of the intramedullary nail 12 to avoid an unintended disassembling of the coupling unit 14 and its drive member 58 and pin 56.

Upon moving of the coupling unit 14 towards the distal portion 22 of the intramedullary nail 12, the coupling unit 14 (particularly, the drive member 58 of the coupling unit 14) urges the pin 56 in the direction of the longitudinal axis 44 of the proximal portion 20 towards the distal portion 22 of the intramedullary nail 12. The pin 56 of the coupling unit 14 thus slides within the guiding structure 48 towards the lag screw 16. In a final position (as shown in FIG. 2), the pin 56 engages within one of the grooves 34 of the lag screw 16 to prevent rotation of the lag screw 16 about its longitudinal axis.

As illustrated in FIGS. 1 and 2, the laterally arranged, eccentric pin 56 allows an engagement within a groove 34 of the lag screw 16. The medial cannulation 66 formed by the canal 64 of the intramedullary nail 12, the central through hole of the drive member 58 and the bore 46 of the proximal portion 20 allows the simultaneous inserting of a guide wire.

During a surgical procedure, the intramedullary nail 12 is positioned and located in the intramedullary canal of a bone, e.g., the femur. Then, a hole is bored transversally through the femur, the neck of the femur and into the head thereof for receiving the lag screw 16. Then, the lag screw 16 is screwed into position through the transverse bore 26 of the intramedullary nail 12 by operating a tool, e.g, a screw driver, such that one of the longitudinal grooves 34 of the lag screw 16 is aligned in the uppermost position. The drive member 58 of the coupling unit 14, which is preassembled within the proximal portion 20 of the intramedullary nail 12, is then turned downwards (i.e., in the direction of the longitudinal axis 44 of the proximal portion 20 towards the distal portion 22 of the intramedullary nail 12) with a screw driver until the lower end of the pin 56 is engaged within one of the grooves 34 of the lag screw 16.

Provided that the coupling unit 14 is not completely tightened (i.e., the drive member 58 of the coupling unit 14 is not completely tightened), the lag screw 16 has the facility to slide within the transverse bore 26 only in a lateral direction (to the right in FIGS. 1 and 2) but is locked against rotation about its longitudinal axis. As the lag screw 16 is held against rotation by the coupling unit 14 (i.e., by the pin 56 of the coupling unit 14), it merely slides through the transverse bore and draws the head of the femur into close engagement with the rest of the bone. Due to the rising ramp of the groove 34 of the lag screw 16, an uncontrolled medial sliding (to the left in FIGS. 1 and 2) of the lag screw 16 within the intramedullary nail 12 is prevented.

FIGS. 3 to 7 show another embodiment of a proximal portion with an alternative coupling unit embodiment, that can be adapted as needed (e.g., in terms of shape, length, width, thickness, etc.) for use in the intramedullary nail 12 of the implant system 10 shown in FIG. 1.

Figure 3:
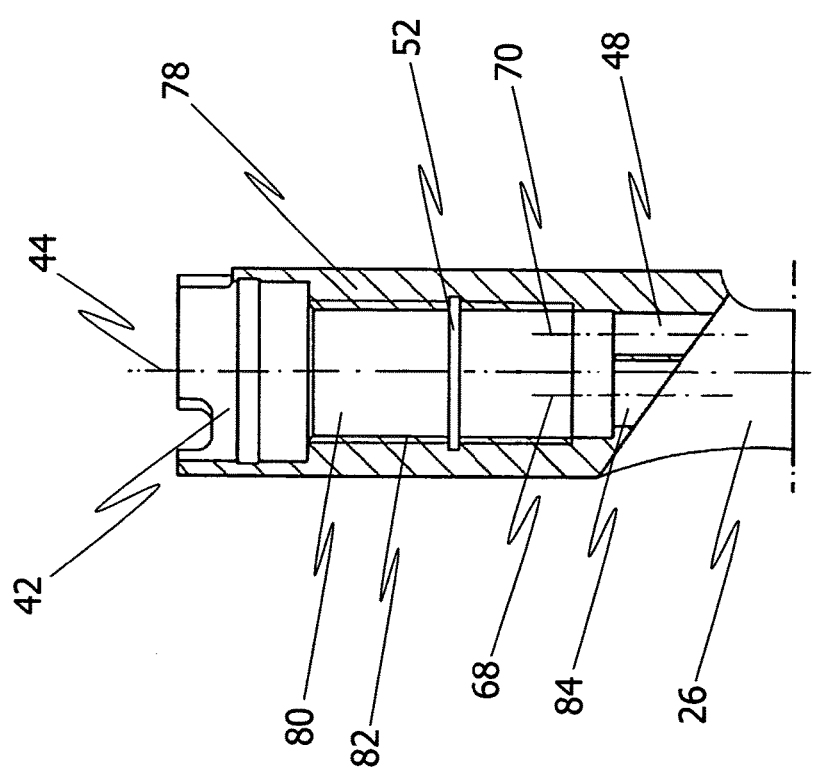
FIG. 3 is a cross-sectional view of an alternative embodiment of the proximal portion of an intramedullary nail.

FIG. 3 illustrates a cross-sectional view of the alternative embodiment of the proximal portion 78 of the intramedullary nail. The proximal portion 78 includes a central bore 80 having an internal thread 82. The proximal portion 78 further includes the recess portion 52 in form of the groove 52 for receiving the retainer 54 within the central bore 80. Moreover, the proximal portion 78 also includes the recess 42 for receiving an end cap or a tool, such as a holding instrument or targeting instrument (not shown in FIG. 3) at the upper end of the proximal portion 78.

As shown in FIG. 3, the guiding structure 48 is formed as a bore 48 located at the lateral side (right-hand side in FIG. 3) of the intramedullary nail. The guiding structure 48 terminates at its upper end in the central bore 80 of the proximal portion 78 and at its lower end in the transverse bore 26. Also in this present embodiment, the term "lower end" means that end which is nearer to the distal portion of the intramedullary nail, and the term "upper end" is the opposite of the lower end. As further illustrated in FIG. 3, the proximal portion 78 includes a bore 84 which is arranged adjacent to the guiding structure 48. The bore 84 of the proximal portion 78 also terminates at its upper end in the central bore 80 and at its lower end in the transverse bore 26 of the intramedullary nail. Further, the bore 84 defines the first axis 68 and the guiding structure 48 defines the second axis 70, wherein the first axis 68 and the second axis 70 are substantially parallel to the longitudinal axis 44 of the proximal portion 78 and are spaced apart from each other (here: spaced apart from each other in the transverse direction), as shown in FIG. 3.

FIG. 4 illustrates a bottom view a), a side view b), and a top view c) of an alternative pin embodiment having a base member 86 in the form of a plate 86 on which the pin 56 is arranged. In the present embodiment, the pin 56 is integrally formed with the plate 86 as a one-piece structure. The pin 56 is configured as generally described above with respect to FIGS. 1 and 2. The plate 86 has a circular shape and a through hole 88 for receiving a surgical wire or a guiding wire. The pin 56 and the through hole 88 are eccentrically arranged on the plate 86.

The plate 86 further has a holding portion 90. The holding portion 90 is arranged on the upper surface opposite to the lower surface on which the pin 56 is arranged. The holding portion 90 extends from the plate 86 and has a L-shape in cross-section as shown in the side view b) of FIG. 4. Further, the holding portion 90 forms an arc along the outer peripheral side of the plate 86 as illustrated in the top view c) of FIG. 4. For this purpose, the arc formed by the holding portion 90 may extend over 180° or less. Thus, the plate 86 and the holding portion 90 thereof form a circular groove 92 for receiving a part of a drive member as described hereinafter.

Referring to FIG. 5, there is shown a side view of another embodiment of a drive member 94 in form of a short bolt. The drive member 94 has an external thread 96 on its outer peripheral surface 98. The external thread 96 of the drive member 94 is interrupted by a circumferential groove 97. The circumferential groove 97 may receive a ring (not shown in FIG. 5) made of synthetic material. The drive member 94 further includes a drive transmitting portion 100. The drive transmitting portion 100 is formed as a flange arranged on the drive member 94, wherein the diameter of the drive transmitting portion 100 is slightly greater than the diameter of a shaft portion 102 of the drive member 94. Thus, a circumferential step 104 is defined by the drive transmitting portion 100 and the shaft portion 102 of the drive member 94. The drive transmitting portion 100 can movably engage with the holding portion 90 of the plate 86, wherein the step 104 of the drive member 94 engages within the circular groove 92 of the holding portion 90. The drive member 94 further comprises a central through hole 106 for receiving a guide wire and a recess 108 (e.g., in the form of a hexalobular internal driving feature or internal hexagon) for receiving a tool, such as a screwdriver, a wrench, or the like.

Figure 7:
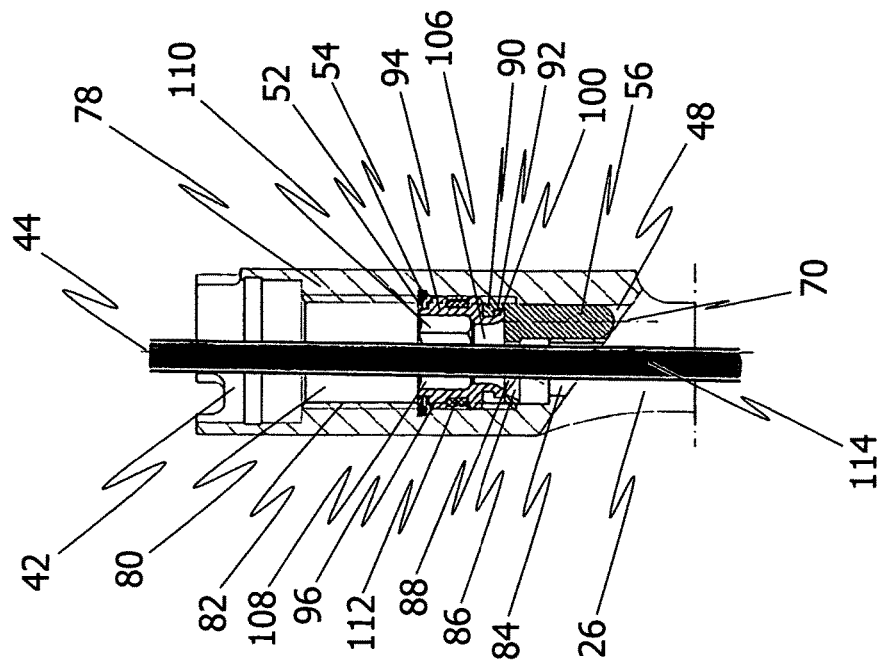
FIG. 7 is a cross-sectional view of the assembly shown in FIG. 6 including a guide wire
Figure 6:
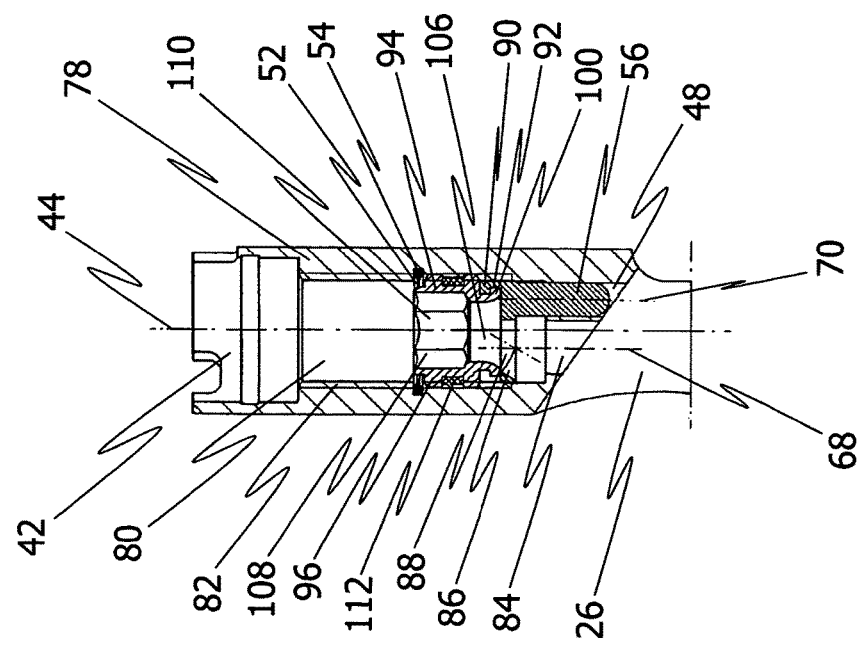
FIG. 6 is a cross-sectional view of the alternative embodiment of the proximal portion shown in FIG. 3 including the pin embodiment shown in FIG. 4 and the drive member embodiment shown in FIG. 5.

As illustrated in FIGS. 6 and 7, a coupling unit 110 is formed by the drive member 94 and the plate 86 having the pin 56, wherein the drive member 94 is movably connected to the plate 86 as described above. Further, the coupling unit 110, i.e, the drive member 94 and the plate 86 with the pin 56, is preassembled within the proximal portion 78 of the intramedullary nail. The guiding structure 48 of the proximal portion 78 of the intramedullary nail has a diameter which is slightly larger than the diameter of the pin 56, such that an optimal guiding and sliding respectively of the pin 56 within the bore 48 is guaranteed. As shown in FIG. 6, the pin 56 of the coupling unit 110 is located within the guiding structure 48 in the preassembled configuration. Moreover, the external thread 96 of the drive member 94 of the coupling unit 110 mates with the internal thread 82 of the central bore 80 of the proximal portion 78 of the intramedullary nail, such that the entire coupling unit 110 is captively held and movably arranged within the proximal portion 78 of the intramedullary nail. Thus, the height adjustment of the coupling unit 110, and therewith of the pin 56, is driven by the drive member 94, as generally described above with respect to FIGS. 1 and 2 and hereinafter. To avoid an unintended loosening of the coupling unit 110, the driving member 94 of the coupling unit 110 has a ring 112 made of synthetic material arranged in the circumferential groove 97 of the drive member 94 as shown in FIGS. 6 and 7. Furthermore, the retainer 54 is positioned and engaged into the recess portion 52 formed as groove 52 within the central bore 80 of the proximal portion 78 of the intramedullary nail to avoid an unintended disassembling of the coupling unit 110 or of its parts (drive member 94 and plate 86 with pin 56). Thus, the retainer 54 functions as a limiter which limits the range of motion of the coupling unit 110 in the proximal direction.

As shown in FIGS. 6 and 7, the drive transmitting portion 100 of the drive member 94 engages on the holding portion 90 of the plate 86. The plate 86 is centrally inserted within the proximal portion 78 of the intramedullary nail, providing rotational stability of the pin 56 of the coupling unit 110. Thus, rotation of the drive member 94 of the coupling unit 110 causes movement of the pin 56, which is slidably received in the guiding structure 48, in the direction of the longitudinal axis 44 of the proximal portion 78 of the intramedullary nail. The rotation of the drive member 94 is performed by a tool such as a screw driver or the like which engages within the recess 108 of the drive member 94. Upon moving of the coupling unit 110 along the longitudinal axis 44 of the proximal portion 78 of the intramedullary nail, the coupling unit 110 (particularly, the drive member 94 of the coupling unit 110) urges the pin 56 through the guiding structure 48 in the direction of the longitudinal axis 44 towards the distal portion of the intramedullary nail, such that the pin 56 engages within a groove of the lag screw to prevent rotation of the lag screw about its longitudinal axis.

As further illustrated in FIGS. 6 and 7, the channel of the intramedullary nail, the bore 84 of the proximal portion 78 of the intramedullary nail, the through hole 88 of the plate 86, the through hole 106 of the drive member 94, and the central bore 80 of the proximal portion 78 define a cannulation. A guide wire 114 may be inserted through the cannulation as shown in FIG. 7.

Figure 8:
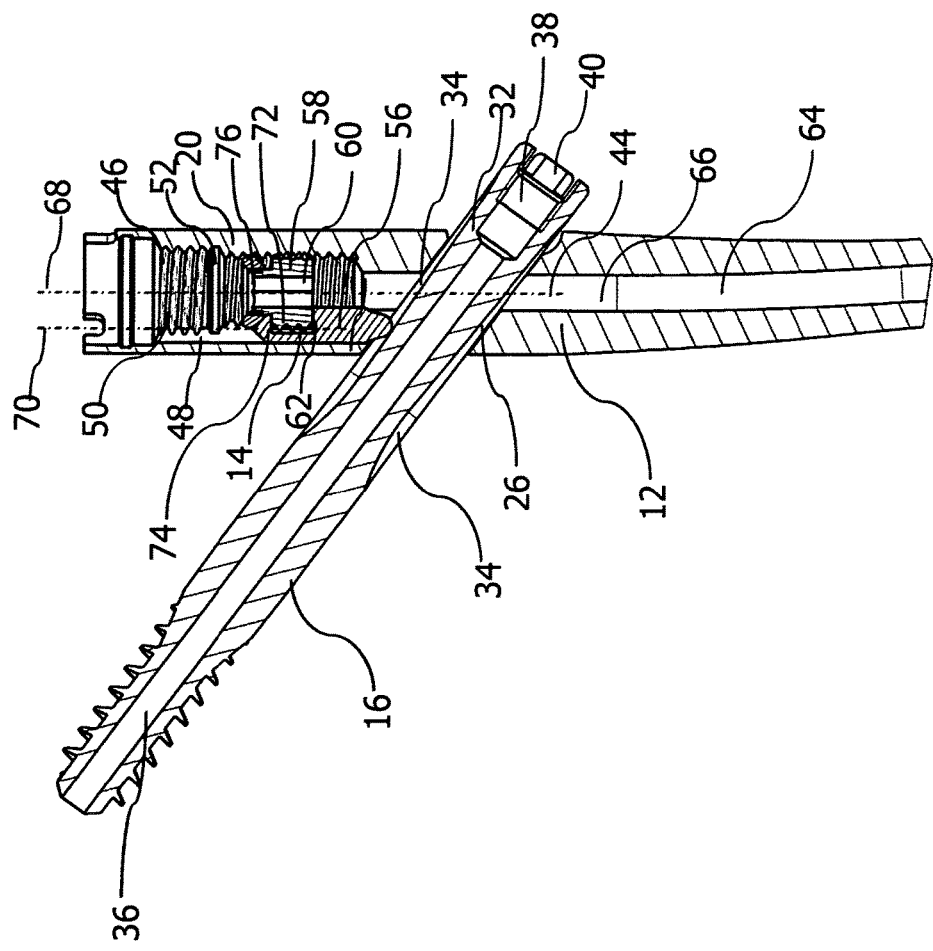
FIG. 8 is a cross-sectional view of an alternative embodiment of the implant system.

FIG. 8 illustrates a cross-sectional view of an alternative embodiment of a proximal portion 20 of the intramedullary nail 12 of the implant system 10 shown in FIGS. 1 and 2. The proximal portion 20 of the intramedullary nail 12 comprises the bore 46 defining the first axis 68 and the guiding structure 48 defining the second axis 70 as shown in and generally described above with reference to FIGS. 1 and 2. The first axis 68 of the bore 46 of the proximal portion 20 and the second axis 70 of the guiding structure 48 are substantially parallel to the longitudinal axis 44 of the proximal portion 20 of the intramedullary nail 12 and are spaced apart from each other. As described above with reference to FIGS. 1 and 2, the second axis 70 of the guiding structure 48 is oriented eccentrically with respect to the longitudinal axis 44 of the proximal portion 20. The intramedullary nail 12 further includes the coupling unit 14 having the pin 56 which is eccentrically arranged on the drive member 58 as shown in and generally described above with reference to FIGS. 1 and 2.

As shown in FIG. 8, the first axis 68 of the bore 46 of the proximal portion 20 coincides with the longitudinal axis 44 of the proximal portion 20. Thus, the bore 46 of the proximal portion 20 is located, in this case, centrally with respect to the longitudinal axis 44 of the proximal portion 20 of the intramedullary nail 12. In the present embodiment illustrated in FIG. 8, the guiding structure 48 of the proximal portion 20 is located at the medial side of the intramedullary nail 12. The guiding structure 48 is configured to slidably receive the cylindrical pin 56 of the coupling unit 14, such that the pin 56 can engage within a groove 34 of a bone fastener 16 configured to penetrate the transverse bore 26 of the intramedullary nail 12. As shown in FIG. 8, the pin 56 of the coupling unit 14 is therefore arranged at the medial side of the intramedullary nail (in FIG. 8, the medial side of the intramedullary nail 12 is on the left side of the drawing). Further, the pin 56 defines a longitudinal axis intersecting the longitudinal axis of the lag screw 16.

Upon moving of the coupling unit 14 towards the distal portion 22 of the intramedullary nail 12, the coupling unit 14, particularly the drive member 58 of the coupling unit 14, urges the pin 56 in the direction of the longitudinal axis 44 of the proximal portion 20 towards the distal portion 22 of the intramedullary nail 12. The pin 56 of the coupling unit 14 thus slides within the guiding structure 48 towards the lag screw 16. In a final position (as shown in FIG. 8), the pin 56 engages at the medial side of the intramedullary nail 12 within a groove 34 of the lag screw 16 to prevent rotation of the lag screw 16 about its longitudinal axis and to provide a defined sliding of the lag screw 16 within the transverse bore 26 of the proximal portion 20.

Figure 9:
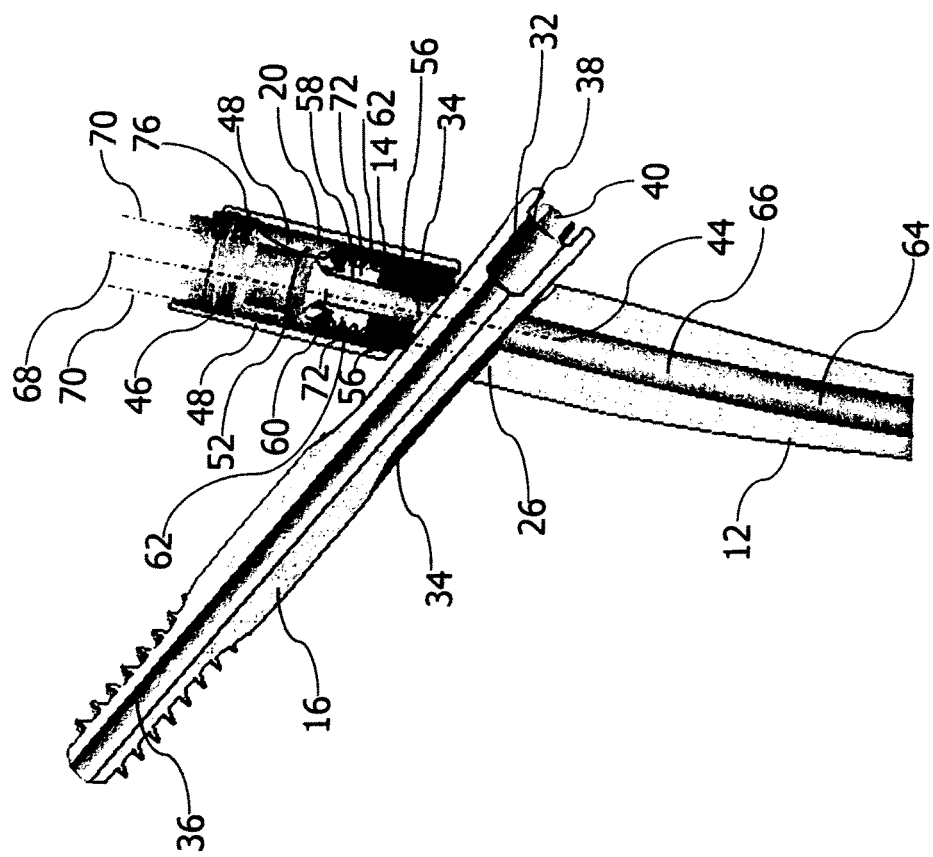
FIG. 9 is a cross-sectional view of a further alternative embodiment of the proximal portion of the implant system.

FIG. 9 illustrates a cross-sectional view of an alternative embodiment of a proximal portion 20 of the intramedullary nail 12 of the implant system 10 as shown in FIGS. 1 and 2. The intramedullary nail 12 shown in FIG. 9 comprises the proximal portion 20, the coupling unit 14 and the bone fastener 16 as shown in and generally described above with reference to FIGS. 1 and 2. Further, the intramedullary nail 12 has the transverse bore 26. The proximal portion 20 defines the longitudinal axis 44 as generally described above with reference to FIGS. 1 and 2.

In the present embodiment the proximal portion 20 of the intramedullary nail 12 includes the bore 46 defining a bore axis 68 and two guiding structures 48, wherein each guiding structure defines a guiding axis 70. As shown in FIG. 9, the bore axis 68 of the bore 46 and the guiding axes 70 are substantially parallel to the longitudinal axis 44 of the proximal portion 20 of the intramedullary nail 12 and are spaced apart from each other. The coupling unit 14 is adapted to be movably arranged within the proximal portion 20 of the intramedullary nail 12 as shown in and generally described above with reference to FIGS. 1 and 2. The coupling unit 14 includes, in this embodiment, two substantially cylindrical pins 56 and the drive member 58. As shown in FIG. 9, one guiding structure is located at the lateral side (right-hand side of the drawing in FIG. 9) and the other guiding structure 48 is located at the medial side (left-hand side in the drawing of FIG. 9) of the intramedullary nail 12. As illustrated in FIG. 9, one pin 56 is arranged at both of the lateral side and the medial side of the intramedullary nail. In other words, one pin 56 is at the lateral side and one further pin 56 is at the medial side of the intramedullary nail 12. Thus, the present embodiment is a combination of the embodiments shown in FIGS. 1, 2 and 8. Further, each guiding structure is configured to slidably receive one of the substantially cylindrical pins 56, such that the pins 56 can engage within a (e.g., one single) groove 34 of the bone fastener 16 which is configured to penetrate the transverse bore 26 of the intramedullary nail 12.

As shown in FIG. 9, the pins 56 are arranged substantially along a direction of the longitudinal axis 44 of the proximal portion 206. Alternatively, the pins 56 may be shifted with respect to the longitudinal axis 44 and may be located in a region at the lateral and medial side of the intramedullary mail 12 respectively. Upon moving of the coupling unit 14 towards the distal portion 22 of the intramedullary nail 12, the coupling unit (particularly, the drive member 58 of the coupling unit 14) urges the two pins 56 in the direction of the longitudinal axis 44 of the proximal portion 20 towards the distal portion 22 of the intramedullary nail 12. The pins 56 of the coupling unit 14 thus slide within the guiding structures 48 toward the lag screw 16. In a final position (as shown in FIG. 9) the pins 56 engage within a (e.g., one single) groove 34 of the lag screw 16 to prevent rotation of the lag screw 16 about its longitudinal axis and to provide a high mechanical load stability of the construct of intramedullary nail 12, coupling unit 14 and bone fastener 16 within the body of the patient.

Figure 10:
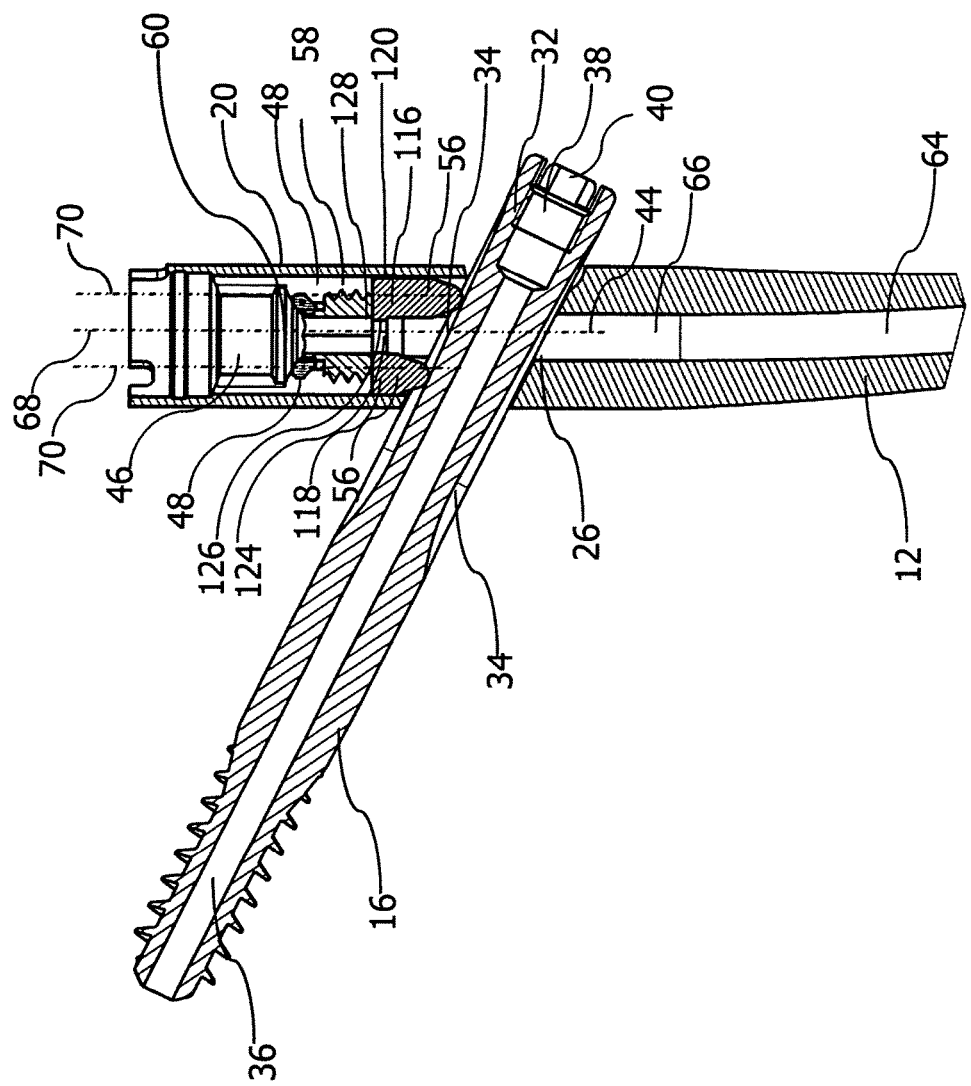
FIG. 10 is a cross-sectional view of an alternative embodiment of the proximal portion of the implant system.
Figure 11:
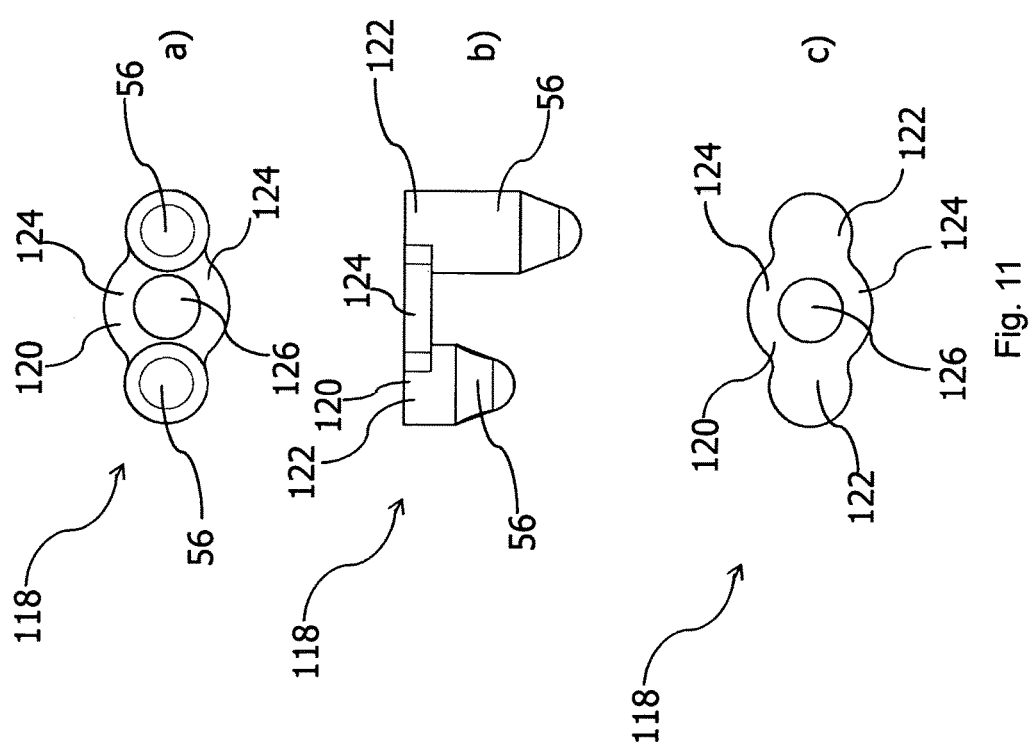
FIG. 11 shows top, side and bottom views of the alternative pin embodiment shown in FIG. 10.

FIGS. 10 and 11 show another embodiment of a proximal portion within an alternative coupling unit embodiment, that can be adapted as needed (e.g., in terms of shape, length, width, thickness, etc.) for use in the intramedullary nail 12 of the implant system 10 shown in FIG. 1.

FIG. 10 illustrates a cross-sectional view of the alternative proximal portion 20 of the intramedullary nail 12. The proximal portion 20 of the intramedullary nail 12, the drive member 58 and the bone fastener 16 are configured as shown in and generally described above with reference to FIGS. 1, 2, 8 and 9. The proximal portion 20 of the intramedullary nail 12 defines the longitudinal axis 44. Further, the proximal portion 20 includes the bore 46 defining a bore axis 68 which is coaxial with the longitudinal axis 44 of the proximal portion 20, i.e., the bore 46 is centrally arranged in the proximal portion 20 of the nail 12 with respect to the longitudinal axis 44 of the proximal portion 20.

In the present embodiment, the proximal portion 20 again includes two guiding structures 48, wherein each guiding structure 48 defines a guiding axis 70. The bore axis 68 and the guiding axes 70 are substantially parallel to the longitudinal axis 44 of the proximal portion 20 of the intramedullary nail 12 and are spaced apart from each other as shown in FIG. 10.

Further, the implant system includes a coupling unit 116 having the drive member 58 as shown in and generally described above with reference to FIGS. 1, 2, 8 and 9. The coupling unit 116 comprises an alternative pin embodiment 118 including two substantially cylindrically pins 56 as generally described above with reference to FIGS. 1, 2, 8 and 9. The pin embodiment 118 of the coupling unit 116 is described with reference to FIG. 11 in more detail below.

As shown in FIG. 10, the guiding structures 48 are formed as grooves. One guiding structure 48 is located at the lateral side (right-hand side in FIG. 10) and the other guiding structure 48 is located at the medial side (left-hand side in FIG. 10) of the intramedullary nail 12. Each guiding structure 48 is configured to slidably receive one of the pins 56 of the pin embodiment 118 of the coupling unit 116, such that the pins 56 can engage within the groove 34 of the bone fastener 16 which is configured to penetrate the transverse bore 26 of the intramedullary nail 12. As illustrated in FIG. 10, one pin 56 is arranged at both of the lateral side and the medial side of the intramedullary nail. In other words, one pin 56 is at the lateral side and one pin is at the medial side of the intramedullary nail.

FIG. 11 illustrates a bottom view a), a side view b), and a top view c) of the alternative pin embodiment 118 used with the drive member 58, which both form the coupling unit 116 as inserted in the proximal portion 20 of the intramedullary nail 10 as shown in the embodiment of FIG. 10. The pin embodiment 118 has a base member 120 in the form of a plate 120 on which two pins 56 are arranged. In the present embodiment, each pin 56 is integrally formed with the plate 120. Each pin 56 is configured as generally described above with reference to FIGS. 1 and 2. The plate 120 has two plate segments 122 with a substantially circular shape. The two plate segments 122 of plate 120 are connected with each other by two curved arms 124, such that the two arms 124 form a through hole 126 for receiving a surgical wire or a guiding wire. Further, the through hole 126 is centrally arranged on the base member 120. As shown in FIG. 11, each pin 56 is arranged on a corresponding plate segment 122 of the base member 120 respectively. Thus, the pins 56 are arranged opposite to each other and extend in the same direction from the base member 120. As further shown in FIG. 11, the pins have a different length in its longitudinal direction. The length of the pins 56 can be adapted as needed for use in the proximal portion 20 of the intramedullary nail 12 of the implant system shown in FIG. 10.

With reference to FIG. 10, the pin embodiment 118 is inserted in the proximal portion 20 of the intramedullary nail 12, such that each pin 56 is received by a guiding structure 48 of the proximal portion 20. In the present embodiment, the pin 56 with the shorter length is received by the guiding structure 48 which is located at the medial side (left-hand side in FIG. 10) of the intramedullary nail 12. Further, the pin 56 having the longer length is received by the guiding structure 48 which is located at the lateral side (right-hand side in FIG. 10) of the intramedullary nail 12. The drive member 58 of the coupling unit 116 includes a drive transmitting portion 128 which engages on the top surface of the base plate 120 of the pin embodiment 118. Thus, as illustrated in FIG. 10, the coupling unit 116 is formed by the drive member 58 and the base member 120 having the pins 56, wherein the drive member 58 is movably connected to the base member 120. Further, the coupling unit 116, i.e., the drive member 58 and the base member 120 with the pins 56, is preassembled within the proximal portion 20 of the intramedullary nail 12. The guiding structures 48 of the proximal portion 20 of the intramedullary nail 12 are formed as open bores (e.g., c-shaped grooves) and have a diameter which is slightly larger than the diameter of each pin 56, such that an optimal guiding and sliding respectively of the pins 56 within the guiding structures 58 is guaranteed.

As shown in FIG. 10, the drive transmitting portion 128 of the drive member 58, which is, in this case, the bottom surface of the drive member 58, engages on the base member 120 of the pin embodiment 118. The base member 120 is centrally inserted within the proximal portion 20 of the intramedullary nail 12, providing rotational stability of the pins 56 of the coupling unit 116. Thus, rotation of the drive member 58 of the coupling unit 116 causes movement of the pins 56, which are slidably received in the guiding structures 48, in the direction of the longitudinal axis 44 of the proximal portion 20 of the intramedullary nail 12. The rotation of the drive member 58 is performed by a tool such as a screw driver or the like which engages within a recess of the drive member as generally described above with reference to FIGS. 1 and 2. Upon moving of the coupling unit 116 along the longitudinal axis 44 of the proximal portion 20 of the intramedullary nail 12, the coupling unit 116 (particularly, the driving member 58 of the coupling unit 116) urges the two pins 56 through the corresponding guiding structure 48 in the direction of the longitudinal axis 44 towards the distal portion 22 of the intramedullary nail 12, such that the pins 56 engage within a (e.g., one) groove of the bone fastener 16. Thus, rotation of the bone fastener about its longitudinal axis is prevented and a high mechanical load stability of the construct of intramedullary nail, coupling unit and bone fastener inserted through the transverse bore 26 of the intramedullary nail 12 and into bone within the body of the patient is provided.

As further shown in FIG. 10, the channel 64 of the intramedullary nail 12, the bore 46 of the proximal portion 20 of the intramedullary nail 12, the through hole 126 of the base member 120 of the pin embodiment 118, the through hole 60 of the drive member 58 define a cannulation 66. A surgical wire or a guide wire (not shown in FIG. 10) may be inserted through the cannulation 66.

Figure 12:
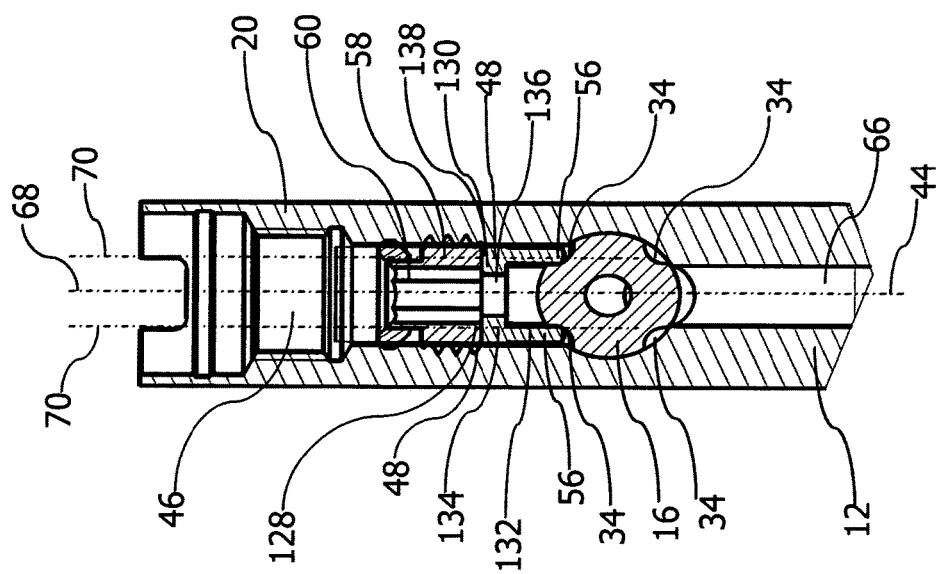
FIG. 12 is a cross-sectional view of an alternative embodiment of the proximal portion of the implant system.
Figure 13:
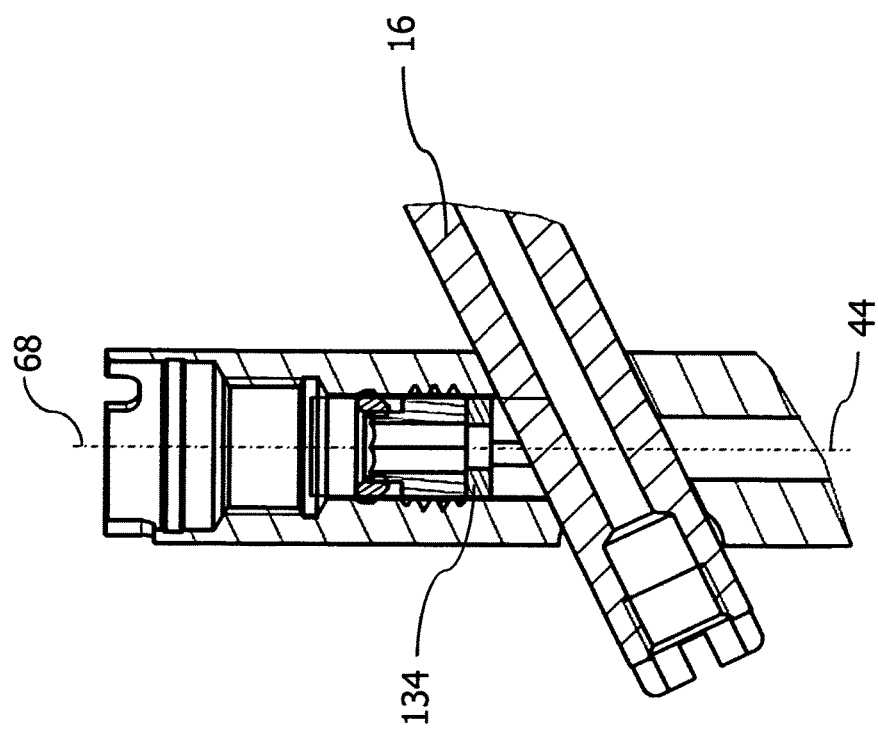
FIG. 13 is a cross-sectional view perpendicular to the cross-sectional view of FIG. 12.
Figure 14:
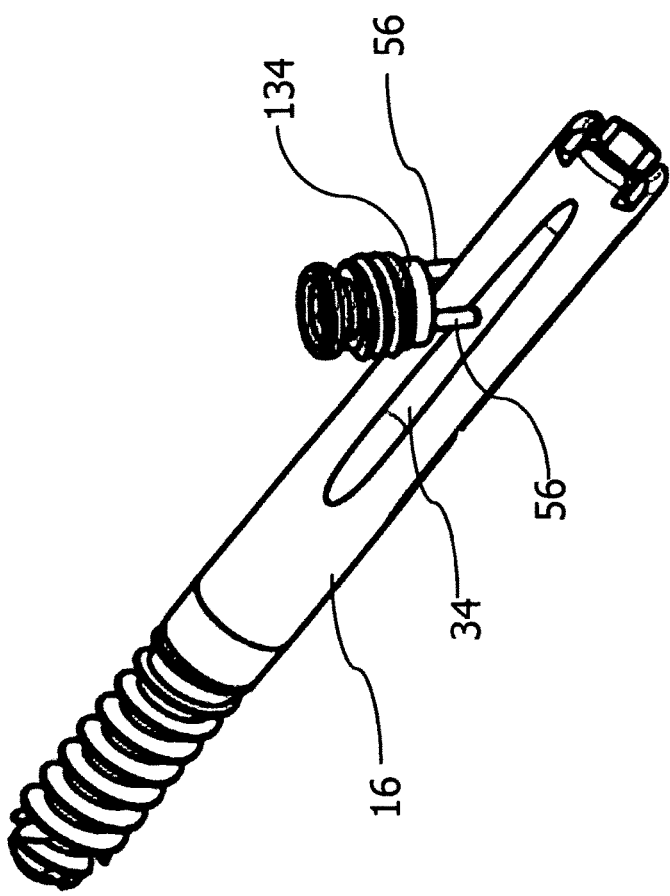
FIG. 14 is a perspective view of the embodiment of FIG. 12 wherein the intramedullary nail has been omitted.

FIGS. 12 to 14 show a still further embodiment of an implant system. As illustrated in the cross-sectional view of FIG. 12, the proximal portion 20 of the intramedullary nail 12, the drive member 58 and the bone fastener 16 are configured as shown in and generally described above with reference to FIGS. 1, 2, 8, 9 and 10. Thus, the proximal portion 20 of the intramedullary nail 12 defines the longitudinal axis 44 and includes the bore 46 defining the bore axis 68 which is, in this case, coaxial with the longitudinal axis 44 of the proximal portion 20, i.e., the bore 46 is centrally arranged in the proximal portion 20 with respect to the longitudinal axis 44 of the proximal portion 20.

In the present embodiment, the proximal portion also includes the two guiding structures 48, wherein each guiding structure 48 defines a guiding axis 70. The bore axis 68 and the guiding axes 70 are substantially parallel to the longitudinal axis 44 of the proximal portion 20 of the intramedullary nail 12 and are spaced apart from each other as shown in FIG. 12.

In the present embodiment, the implant system includes an alternative coupling unit embodiment that can be adapted as needed (e.g., in terms of shape, length, width, thickness, etc.) for use in the proximal portion 20 of the intramedullary nail 12 shown in FIG. 12. The alternative coupling unit 130 includes the drive member 58 as shown in and generally described above with reference to FIGS. 1, 2, 8, 9 and 10. The coupling unit 130 further comprises an alternative pin embodiment 132 including two substantially cylindrical pins 56 as generally described above with reference to FIGS. 1, 2, 8, 9 and 10.

The pin embodiment 132 of the coupling unit 130 has a base member 134 in form of a plate 134 on which the two pins 56 are arranged. In the present embodiment, each pin 56 is integrally formed with the plate 134. Each pin 56 is configured as generally described above with reference to FIGS. 1 and 2. The plate 134 has a circular shape and through hole 136 for receiving a surgical wire or a guiding wire (not shown in FIG. 12). As shown in FIG. 12, the through hole 136 is centrally arranged on the base member 134. The pins 56 are eccentrically arranged on the plate 134. Further, the pins 56 are arranged opposite to each other and extend in the same direction from the base member 134. In the present embodiment, the pins 56 are positioned on the base member 134 along a direction of a diameter of the circular plate 134 that perpendicularly crosses the longitudinal axis 44. Alternatively, the pins 56 can be shifted for example in a parallel manner with respect to a line defined by that diameter of the circular plate 134, e.g., shifted in a direction which is substantially perpendicular to the diameter of the circular plate 134. In this case, the pins 56 may lie on a line which is parallel to the diameter of the circular plate 134. As further shown in FIG. 12, each pin 56 is arranged on the plate 134 near the outer periphery of the base member 134.

As illustrated in FIG. 12, the guiding structures 48 are located at opposite sides with respect to the longitudinal axis of the bone fastener 16 which is configured to penetrate the transverse bore 26 of the intramedullary nail 12. Thus, the guiding structures 48 can be located in a central position with respect to the proximal portion 20 (as shown in FIG. 12), or alternatively, at the medial side or at the lateral side of the intramedullary nail 12. Thus, the two pins 56 can alternatively be arranged closer to one of the lateral side and the medial side of the intramedullary nail 12. In other words, the pins 56 can be at the lateral side or at the medial side of the intramedullary nail 12.

The pin embodiment 132 is inserted in the proximal portion 20 of the intramedullary nail 12, such that each pin 56 is received by a guiding structure 48 of the proximal portion 20. The drive member 58 of the coupling unit 130 includes a drive transmitting portion 138 which engages on the top surface of the plate 134 of the pin embodiment 132. In this case, the drive transmitting portion 138 is the bottom surface of the drive member 58. Thus, as illustrated in FIG. 12, the coupling unit 130 is formed by the drive member 58 and the base member 134 having the pins 56, wherein the drive member 58 is movably connected to the base member 134. Further, the coupling unit 130, i.e., the drive member 58 and the base member 134 with the pins 56, is preassembled within the proximal portion 20 of the intramedullary nail 12.

As shown in FIG. 12, the drive transmitting portion 138 of the drive member 58 engages on the base member 134 of the pin embodiment 132. The base member 134 is centrally inserted within the proximal portion 20 of the intramedullary nail 12, i.e., centrally inserted within the bore 46 of the proximal portion 20, providing rotational stability of the pins 56 of the coupling unit 130. Thus, rotation of the drive member 58 of the coupling unit 130 causes movement of the pins 56, which are slidably received in the guiding structures 48, in the direction of the longitudinal axis 44 of the proximal portion 20 of the intramedullary nail 12. The rotation of the drive member 58 is performed by a tool as generally described above with reference to FIGS. 1, 2, 8, 9 and 10. Upon moving of the coupling unit 130 along the longitudinal axis 44 of the proximal portion 20 of the intramedullary nail 12, the coupling unit 130 (particularly, the drive member 58 of the coupling unit 130) urges the two pins 56 through the corresponding guiding structure 48 in the direction of the longitudinal axis 44 towards the distal portion of the intramedullary nail 12, such that each pin 56 engages within a dedicated groove 34 of the bone fastener 16. Hence, as shown in FIGS. 12 and 14, the pins 56 of the coupling unit 130 engage within two different grooves 34 of the bone fastener 16. Moreover, upon engagement within the grooves 34, the pins 56 can exert pressure on the lag screw 16 for stabilization purposes. Thus, a rotation of the bone fastener 16 about its longitudinal axis is prevented and a high mechanical load stability of the construct of intramedullary nail, coupling unit and bone fastener inserted through the transverse bore 26 of the intramedullary nail 12 and into bone within the body of the patient is provided.

As stated above, in other embodiments the pins 56 may be shifted out of the central nail plane illustrated in FIG. 12 towards one of the lateral side and the medial side of the intramedullary nail 12. The pins 56 will then lie on a line (the above "diameter") that extends perpendicularly to a plane including the longitudinal axis 44 of the proximal portion 20 and a longitudinal axis of the transverse bore 26, wherein the line is spaced apart from that plane in one of a medial direction and a lateral direction of the intramedullary nail 12. In such case the engagement of two grooves 34 by the two pins 56 may be maintained, although in certain cases the grooves 34 may need to be modified (e.g., as regards their width or number).

As further shown in FIG. 12, the channel 64 of the intramedullary nail 12, the bore 46 of the proximal portion 20 of the intramedullary nail 12, the through hole 136 of the base member 134 of the pin embodiment 132, the through hole 60 of the drive member 58 define a cannulation 66. A surgical wire or a guide wire (not shown in FIG. 12) may be inserted through the cannulation 66.

In an exemplary method for fracture fixation of bone using any of the above or other implant system embodiments, the guide wire 114 (see FIG. 7) is firstly inserted into a marrow cavity of bone. Then, the cannulated intramedullary nail 12 of any of the above or other embodiments is inserted over the guide wire 114 into the marrow cavity of bone. The intramedullary nail comprises a medial side, a lateral side and the proximal portion 20 or 78, the transverse bore 26 and the coupling unit 14, 110, 116 or 130 as generally described above. The guide wire 114 is then removed and a bone fastener 16 is inserted through the transverse bore 26 of the intramedullary nail 12 into bone for stabilization of the bone fracture. Finally, the coupling unit of the intramedullary nail 12 is driven for producing an engagement of the pin 56 with the bone fastener 16 penetrating the transverse bore 26 of the intramedullary nail 12, thereby preventing rotation of the bone fastener 16.

Since the proximal portion of the intramedullary nail and the coupling unit having the drive member and the pin are configured as described above, the coupling unit can be preassembled or preloaded within the intramedullary nail, while allowing a simultaneous inserting/passage of a guide wire. The channel of the intramedullary nail, the bore(s) of the proximal portion of the intramedullary nail and the through hole(s) of the coupling unit (which together define a cannulation) may be substantially aligned to permit insertion of a guide wire completely through the preassembled unit and the intramedullary nail. Thus, a guide wire can be used to guide the intramedullary nail, including the preassembled coupling unit, into the intramedullary canal of, e.g., the femur. Therefore, the coupling unit has not to be assembled intraoperatively. Consequently, the operation steps that need to be performed by a surgeon are reduced, whereby the surgical procedure and the implantation of the intramedullary nail within an intramedullary canal of a femur is facilitated and simplified. Due to this fact, the operation time is reduced. Since the intramedullary nail is provided with the coupling unit (including the pin and the drive member movably connected thereto) that is preassembled into the hollow portion (bore) of the proximal portion of the intramedullary nail, the amount of time associated with implanting the intramedullary nail as well as the number of parts which have to be handled by a surgeon is reduced.

While the one or more guiding structures and/or the one or more pins (i.e., the one or more engagement members) as described herein are substantially located at the lateral or medial side of the intramedullary nail, the one or more guiding structures of the proximal portion of the intramedullary nail and the one or more pins of the coupling unit can be adapted to different applications as needed. Thus, the guiding structures of the proximal portion of the intramedullary nail and the one or more pins of the coupling unit may, for example, be located in an area at the lateral or medial side of the intramedullary nail. Moreover, more, e.g. two or more, pins may be located at one or both of the lateral side and the medial side of the intramedullary nail.

All parts of the implant system described above are easily and cheaply produceable with the current state of machine tools. Moreover, since the pin can engage within a groove of the bone fastener, any modifications or changes of the current bone fasteners are not necessary. Since the guide wires deviate to an eccentric position (e.g., to the medial side) within the intramedullary nail due to the bending of the intramedullary nail, the eccentric arrangement of the pin of the coupling unit and in particular of the bore of the proximal portion of the intramedullary nail facilitates the fence of the guide wire inside the intramedullary nail.

While the rod-shaped body of the intramedullary nail includes a distal portion and a bent portion in the embodiment illustrated in the drawings, the nail body can be adapted as needed (e.g., in terms of shape, length, width, thickness, etc.) for use in orthopaedic surgery for fixation of bone and for insertion into an intramedullary canal of, e.g., a femur. Thus, the intramedullary nail can be adapted to different applications and may thus have a different shape. Moreover, while the threads as shown herein are one start threads, they could also be multiple start threads (e.g., a two-start thread).

While the bone fastener as described herein is formed as a lag screw, the bone fastener can be of any type of, e.g., a femoral neck screw or any kind of blade, and can be adapted to different applications as needed. The bone fasteners may thus have different diameters, lengths, shapes or threads. Further, the bone fastener and the implant described above can generally be made of stainless steel, titanium or any other biocompatible material.

While the above embodiments have exemplarily been described in relation to a bone screw and an intramedullary nail, it will be readily apparent that the techniques presented herein can also be implemented in combination with other types of bone fasteners (such as bone pegs having a rod-like or pin-like shafts, wire-like bone fasteners such as Kirschner wires, etc.) as well as other types of implants (such as bone plates, bone distractors, etc). Accordingly, the present disclosure is not limited to any type of bone fastener or any type of implant.

The features described in the above description taken in conjunction with the accompanying drawings can be readily combined to result in different embodiments. It will thus be apparent that the disclosure described above may be varied in many ways. Such variations are not to be regarded as a departure from the scope of the invention, and all modifications are intended to be included within the scope of the following claims.

The invention claimed is:

1. An implant system for use in orthopaedic surgery for fixation of bone, comprising:
   a bone fastener;
   an intramedullary nail with a medial side, a lateral side and a proximal portion defining a central longitudinal axis, wherein the proximal portion includes an axial bore defining a first axis substantially parallel to the longitudinal axis of the proximal portion and at least one transverse bore having a central longitudinal axis extending from the medial side to the lateral side of the proximal portion configured to receive the bone fastener;

a coupling unit configured to be movably arranged within the axial bore of the proximal portion and the coupling unit having a base member formed at a proximal end thereof, including first and second bone fastener engagement pins extending from the base member each engagement pin having a central longitudinal axis, the first bone fastener engagement pin located at the lateral side of the intramedullary nail and the second bone fastener engagement pin located at the medial side of the intramedullary nail, wherein the medial and lateral sides generally lie within a plane including the central longitudinal axis of the proximal portion and a central longitudinal axis of the transverse bore, the central longitudinal axis of the first and second bone fastener engagement pins lying in the plane;

wherein the first and second bone fastener engagement pins are interconnected by the base member and have distal ends for engaging the bone fastener; and further comprising a first and second guiding structure in the axial bore of the proximal nail portion respectively slidably engaging the first and second bone fastener engagement pins, the first and second guiding structures are formed as a first and second axially extending recesses formed in a wall of the proximal portion axial bore, the axially extending recesses guiding the first and second bone fastener engagement pins in the axial direction into the bone fastener, the engagement of the first and second bone fastener engagement pins and the recesses preventing the rotation of the coupling unit about the central longitudinal axis during axial movement of the coupling unit prior to the first and second bone fastener engagement pins distal ends engaging the bone fastener.

2. The implant system according to claim 1, wherein the proximal portion is adapted to guide the coupling unit with the first and second bone fastener engagement pins have a longitudinal axis extending in a direction substantially parallel to the longitudinal axis of the proximal portion.

3. The implant system according to claim 1, wherein, each axially extending recess defining a central longitudinal axis substantially parallel to the longitudinal axis of the proximal portion.

4. The implant system according to claim 3, wherein the longitudinal axis of the first and second guiding structures are oriented eccentrically with respect to the longitudinal axis of the proximal portion.

5. The implant system according to claim 3, wherein the first and second axially extending recesses are formed as grooves or bores.

6. The implant system according to claim 3, wherein the bore of the proximal portion and the first and second axially extending recesses are arranged adjacent to each other.

7. The implant system according to claim 3, wherein the first and second axially extending recesses are respectively located at the lateral side and the medial side of the intramedullary nail.

8. The implant system according to claim 1, wherein the coupling unit first bone fastener engagement pin and second bone fastener engagement pin lie on a line that extends along the plane including the longitudinal axis of the proximal portion and a longitudinal axis of the transverse bore, wherein the line is spaced apart from the longitudinal axis of the proximal portion in a medial direction and a lateral direction of the intramedullary nail.

9. The implant system according to claim 1, wherein the axial bore of the proximal portion is located at the medial side or at the lateral side of the intramedullary nail or is centrally located with respect to the longitudinal axis of the proximal portion.

10. The implant system according to claim 1, wherein the coupling unit is configured to urge, upon moving of the coupling unit toward a distal portion of the intramedullary nail, the first and second bone fastener engagement pins in the direction of the longitudinal axis of the proximal portion towards the distal portion.

11. The implant system according to claim 1, wherein each of the first and second bone fastener engagement pins define a longitudinal axis intersecting a longitudinal axis of the transverse bore.

12. The implant system according to claim 1, wherein the first and second bone fastener engagement pins are eccentrically arranged on a drive member of the coupling unit.

13. The implant system according to claim 1, wherein the coupling unit includes a drive member for moving the coupling unit within the axial bore of the proximal portion.

14. The implant system according to claim 13, wherein the drive member has an external thread for threadable engagement with the intramedullary nail.

15. The implant system according to claim 14,
wherein the axial bore of the proximal portion of the intramedullary nail includes an internal thread, wherein the external thread of the drive member is configured to mate with the internal thread of the axial bore.

16. The implant system according to claim 13, wherein the drive member further includes a ring arranged in a circumferential groove of the drive member.

17. The implant system according to claim 13, wherein the drive member includes a drive transmitting portion, and the first and second bone fastener engagement pins include a groove arranged in a direction transverse to the longitudinal direction of the first and second bone fastener engagement pins, wherein the drive transmitting portion movably engages within the groove of the first and second bone fastener engagement pins.

18. The implant system according to claim 17, wherein the drive transmitting portion is rotatably supported in the groove of the first and second bone fastener engagement pins.

19. The implant system according to claim 13, wherein the drive member includes a drive transmitting portion, and the first and second bone fastener engagement pins are arranged on a base member, wherein the drive transmitting portion movably engages the base member.

20. The implant system according to claim 1, further comprising a retainer arranged in the proximal portion of the intramedullary nail, wherein the range of motion of the coupling unit in the proximal direction is limited by the retainer.

21. The implant system according to claim 1, further comprising the bone fastener, wherein the first and second bone fastener engagement pins engage the bone fastener to prevent rotation of the bone fastener about a longitudinal axis of the bone fastener.

22. The implant system according to claim 1, wherein the coupling unit is captively held within the proximal portion of the intramedullary nail.

23. The implant as set forth in claim 1, wherein the proximal nail portion has a longitudinally extending part-cylindrical groove open to the axial bore extending along the medial side and along the lateral side of the proximal nail portion and wherein each medial and lateral engagement pin includes a cylindrical portion slidably engaging the respective medial and lateral part-cylindrical grooves.

24. An implant system for use in orthopaedic surgery for fixation of bone, comprising:
an intramedullary nail with a proximal portion defining a central longitudinal axis, wherein the proximal portion includes a bore defining a central longitudinal axis substantially parallel to the central longitudinal axis of the proximal portion and at least one transverse bore having a central longitudinal axis extending from a lateral side to a medial side of the nail;
a bone fastener having a threaded end and an opposite rear portion configured to penetrate the transverse bore and having at least one groove; and
a coupling unit configured to be movably arranged within the bore of the proximal portion and including one or more bone fastener engagement members offset from the proximal portion bore central longitudinal axis configured to engage the at least one groove and to exert pressure on the bone fastener via one or more ramps, the central longitudinal axis of the intramedullary nail intersecting the central longitudinal axis of the transverse bore, a plane containing the central longitudinal axis of the nail and transverse bore also contains a central axis of a guide structure for guiding the one or more bone fastener engagement members, the engagement between the bone fastener engagement members and the guide structure preventing rotation of the coupling unit prior to the bone fastener engagement members engaging the at least one groove.

25. A method of fracture fixation of bone comprising the steps of:
inserting an intramedullary nail with a medial side and a lateral side into a marrow cavity of bone, the intramedullary nail having a traverse bore with a central longitudinal axis extending from the medial side to the lateral side of the nail, wherein the intramedullary nail comprises:
a proximal portion defining a longitudinal central axis, wherein the proximal portion includes an axial bore defining a first axis substantially parallel to the central longitudinal axis of the proximal portion and the transverse bore is configured to receive a bone fastener;
a coupling unit movably arranged within the bore of the proximal portion and including a first and second bone fastener engagement pins, the first pin at the lateral side and the second pin at the medial side of the intramedullary nail, wherein the medial and lateral sides generally lie within a plane including the central longitudinal axis of the proximal portion and the central longitudinal axis of the transverse bore, and wherein the proximal nail portion further comprises a first guiding structure in the axial bore engaging one of the first or second bone fastener engagement pins, the guiding structure comprising first and second axially extending recesses for respectively slidably receiving the first and second bone fastener engagement pins, the first and second recesses open to the proximal portion axial bore;
inserting a bone fastener through the transverse bore of the proximal portion of the intramedullary nail into bone for stabilization of the bone fracture;
driving the coupling unit for producing an engagement of the first and second bone fastener engagement pins with the bone fastener penetrating the transverse bore of the intramedullary nail, thereby preventing rotation of the bone fastener;
wherein the first and second bone fastener engagement pins have different lengths; and
wherein the first and second bone fastener engagement pins are interconnected by a base member, the engagement of the first and second bone fastener engagement pins and the recesses preventing the rotation of the coupling unit about the central longitudinal axis during axial movement of the coupling unit prior to the first and second bone fastener engagement pins distal ends engaging the bone fastener.

26. The method of claim 25, further comprising the steps of:
inserting a guide wire into the marrow cavity of bone, wherein the intramedullary nail is cannulated and inserted over the guide wire into the marrow cavity of bone; and
removing the guide wire after insertion of the intramedullary nail.

27. The implant as set forth in claim 25, wherein the proximal nail portion has a longitudinally extending part-cylindrical groove open to the axial bore extending along the medial side and along the lateral side of the proximal nail portion and wherein each medial and lateral engagement pin includes a cylindrical portion slidably engaging the respective medial and lateral part-cylindrical grooves.

28. An implant system for use in orthopaedic surgery for fixation of bone, comprising:
an intramedullary nail with a medial side, a lateral side and a proximal portion defining a central longitudinal axis, wherein the proximal portion includes an axial bore and a bore extending transverse to the central longitudinal axis configured to receive a bone fastener, the transverse bore having a central longitudinal axis extending from the medial to the lateral side of the nail;
a coupling unit having a body movably arranged within the axial bore of the proximal portion and the body including first and second bone fastener engagement pins offset from the central longitudinal axis, the first bone fastener engagement pin offset from the central longitudinal axis in a lateral direction and the second bone fastener engagement pin offset from the central longitudinal axis in the medial direction of the intramedullary nail, wherein the medial and lateral directions generally lie within a plane including the central longitudinal axis of the proximal portion and the central longitudinal axis of the transverse bore, wherein the coupling unit body has a bore therethrough aligned with the axial bore of the proximal portion of the nail;
wherein the first and second bone fastener engagement pins have different lengths with the first being longer than the second; and
wherein the first and second bone fastener engagement members are interconnected by a base member, wherein the proximal nail portion further comprises an axially extending first and second guiding structure respectively formed on the medial and lateral sides of the axial bore respectively engaging the first and second bone fastener engagement pins, the first and second guiding structure having a central axis lying in the plane, the first and second guiding structures slidably receiving a respective one of the first and second bone fastener engagement pins, the axially extending first and second guiding structures are formed as recesses in a wall of the proximal portion axial bore and are open to the bore, the engagement of the first and second bone fastener engagement members and the first and second guiding structure recesses preventing the rotation of the coupling unit about the central longitudinal axis during axial movement of the coupling unit prior to a distal end of the first and second bone fastener engagement members entering the transverse bore.

29. The implant as set forth in claim 28, wherein the proximal nail portion has a longitudinally extending part-cylindrical groove open to the axial bore extending along the medial side and along the lateral side of the proximal nail portion and wherein each medial and lateral engagement pin includes a cylindrical portion slidably engaging the respective medial and lateral part-cylindrical grooves.

30. An implant system for use in orthopaedic surgery for fixation of bone, comprising:

an intramedullary nail with a medial side, a lateral side and a proximal portion defining a central longitudinal axis, wherein the proximal portion includes an axial bore and a bore having a central longitudinal axis extending transverse to the intramedullary nail central longitudinal axis, the axial bore in the proximal portion intersected by a longitudinally extending guide structure located on a medial or lateral side of the axial bore;

an axially extending bone fastener configured to penetrate the transverse bore, the bone fastener having a least one axially extending groove formed on an outer surface of the bone fastener; and a coupling unit having a body movably arranged within the axial bore of the proximal portion and the body including a bore therethrough aligned with the axial bore in the proximal portion, the coupling unit having one and only one bone fastener engagement pin offset from the central longitudinal axis of the axial bore in one of the lateral direction or the medial direction of the intramedullary nail, wherein the medial and lateral direction generally lie within a plane including the central longitudinal axis of the proximal portion and the central longitudinal axis of the transverse bore, wherein the one and only one bone fastener engagement pin slidably engages one of the medial or lateral guide structures in the proximal portion of the bone nail and guided by the guide structure into the axially extending groove of the bone fastener, the medial or lateral guide structure comprising an axially extending longitudinal recess circumferentially intersecting the proximal portion axial bore, the engagement of the bone fastener engagement pin with the medial or lateral guide structure prevents rotation of the coupling unit prior to the bone fastener engagement pin entering into the axially extending groove of the bone fastener.

* * * * *